United States Patent
Ito

(10) Patent No.: US 11,583,173 B2
(45) Date of Patent: Feb. 21, 2023

(54) LIGHT SOURCE APPARATUS, ENDOSCOPE SYSTEM, AND ILLUMINATION CONTROL METHOD FOR ADJUSTING FIRST AND SECOND ILLUMINATION LIGHT EMITTED FROM FIRST AND SECOND ILLUMINATION LIGHT EMISSION ENDS OF A LIGHT GUIDE

(71) Applicant: OLYMPUS CORPORATION, Tokyo (JP)

(72) Inventor: Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 483 days.

(21) Appl. No.: 16/712,277

(22) Filed: Dec. 12, 2019

(65) Prior Publication Data
US 2020/0113425 A1 Apr. 16, 2020

Related U.S. Application Data

(63) Continuation of application No. PCT/JP2017/022706, filed on Jun. 20, 2017.

(51) Int. Cl.
*A61B 1/06* (2006.01)
*A61B 1/07* (2006.01)
(Continued)

(52) U.S. Cl.
CPC .......... *A61B 1/0676* (2013.01); *A61B 1/0655* (2022.02); *A61B 1/0669* (2013.01);
(Continued)

(58) Field of Classification Search
None
See application file for complete search history.

(56) References Cited

U.S. PATENT DOCUMENTS 4,678,900 A * 7/1987 Nishioka ............ G02B 23/2469
348/E5.038
5,016,975 A 5/1991 Sasaki et al.
(Continued)

FOREIGN PATENT DOCUMENTS

CN 106488733 A 3/2017
JP 61-37226 A 2/1986
(Continued)

OTHER PUBLICATIONS

English translation of International Preliminary Report on Patentability dated Jan. 2, 2020, together with the Written Opinion received in related International Application No. PCT/JP2017/022706.
(Continued)

*Primary Examiner* — John P Leubecker
(74) *Attorney, Agent, or Firm* — Scully, Scott, Murphy & Presser, P.C.

(57) ABSTRACT

A light source apparatus includes a light source optically connectable to a scope including a light guide configured to guide light, and first and second illumination light emission units configured to radiate illumination light based on the guided light on a subject, and a light quantity distribution changing device disposed on an optical path of the light emitted from the light source. The light quantity distribution changing device is configured to control a light quantity of the light brought into each of the first illumination light emission unit and the second illumination light emission unit, so as to change a light quantity distribution of the illumination light radiated on the subject.

14 Claims, 18 Drawing Sheets

(51) Int. Cl.
*G02B 23/24* (2006.01)
*G02B 23/26* (2006.01)
*G02B 26/08* (2006.01)

(52) U.S. Cl.
CPC ............ *A61B 1/07* (2013.01); *G02B 23/2469* (2013.01); *G02B 23/26* (2013.01); *G02B 26/0833* (2013.01)

(56) References Cited

U.S. PATENT DOCUMENTS

| | | |
|---|---|---|
| 6,464,633 B1 | 10/2002 | Hosoda et al. |
| 2002/0156349 A1 | 10/2002 | Yamaki et al. |
| 2005/0211872 A1 | 9/2005 | Kawano et al. |
| 2011/0257483 A1* | 10/2011 | Mizuyoshi ............ G02B 6/425 362/555 |
| 2013/0335544 A1* | 12/2013 | Ookoba ................ A61B 1/06 348/68 |
| 2015/0005575 A1* | 1/2015 | Kobayashi ......... A61B 1/00009 600/103 |
| 2017/0055817 A1* | 3/2017 | Dybiec ............. A61B 1/00006 |
| 2017/0127925 A1 | 5/2017 | Honda et al. |

FOREIGN PATENT DOCUMENTS

| | | |
|---|---|---|
| JP | 61-177419 A | 8/1986 |
| JP | 61-177421 A | 8/1986 |
| JP | 2-152103 A | 6/1990 |
| JP | 4-70710 A | 3/1992 |
| JP | 7-275192 A | 10/1995 |
| JP | 11-305142 A | 11/1999 |
| JP | 2001-235686 A | 8/2001 |
| JP | 2002-119468 A | 4/2002 |
| JP | 2005-275206 A | 10/2005 |
| JP | 2009-273687 A | 11/2009 |
| JP | 2011-224044 A | 11/2011 |
| JP | 2012-95909 A | 5/2012 |
| JP | 2013-83855 A | 5/2013 |
| JP | 2013-88492 A | 5/2013 |
| JP | 2017-113221 A | 6/2017 |
| WO | 2013/002050 A1 | 1/2013 |
| WO | 2015/151956 A1 | 10/2015 |
| WO | 2016/079789 A1 | 5/2016 |
| WO | 2016/189629 A1 | 12/2016 |

OTHER PUBLICATIONS

Chinese Office Action dated Jun. 21, 2021 received in 201780091906.0.
International Search Report dated Sep. 19, 2017 received in PCT/JP2017/022706.
Chinese Office Action dated Jan. 19, 2022 received in 201780091906.0.

* cited by examiner

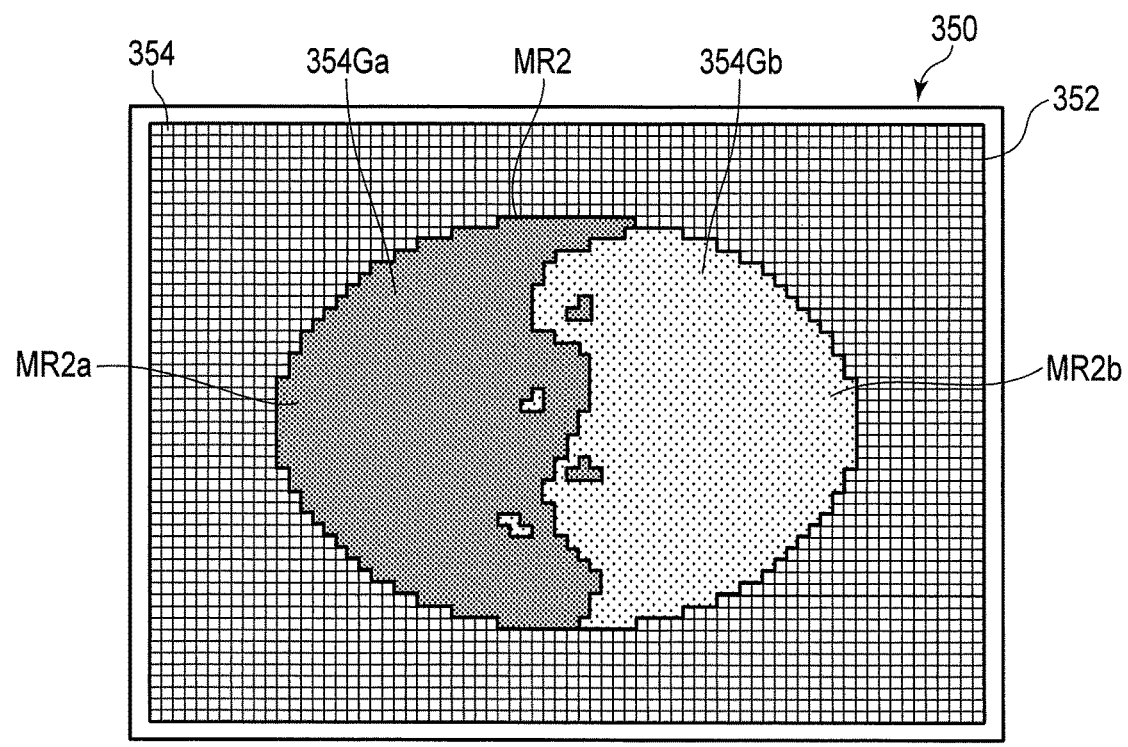
F I G. 9
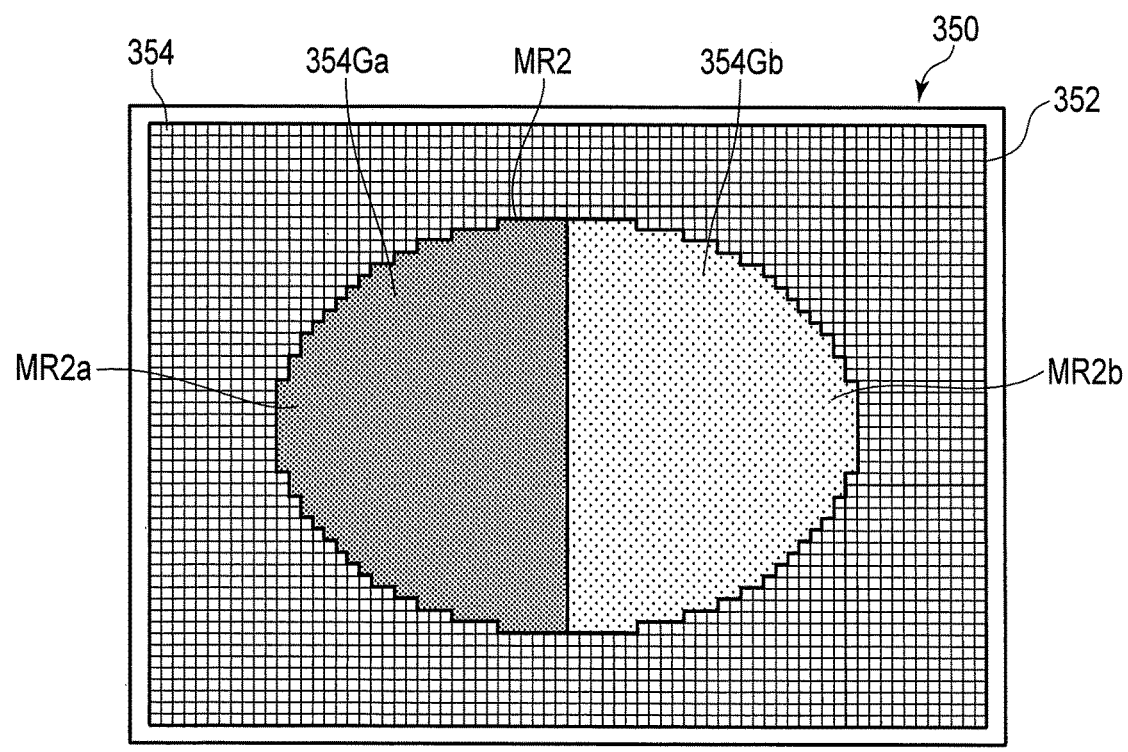
F I G. 9A

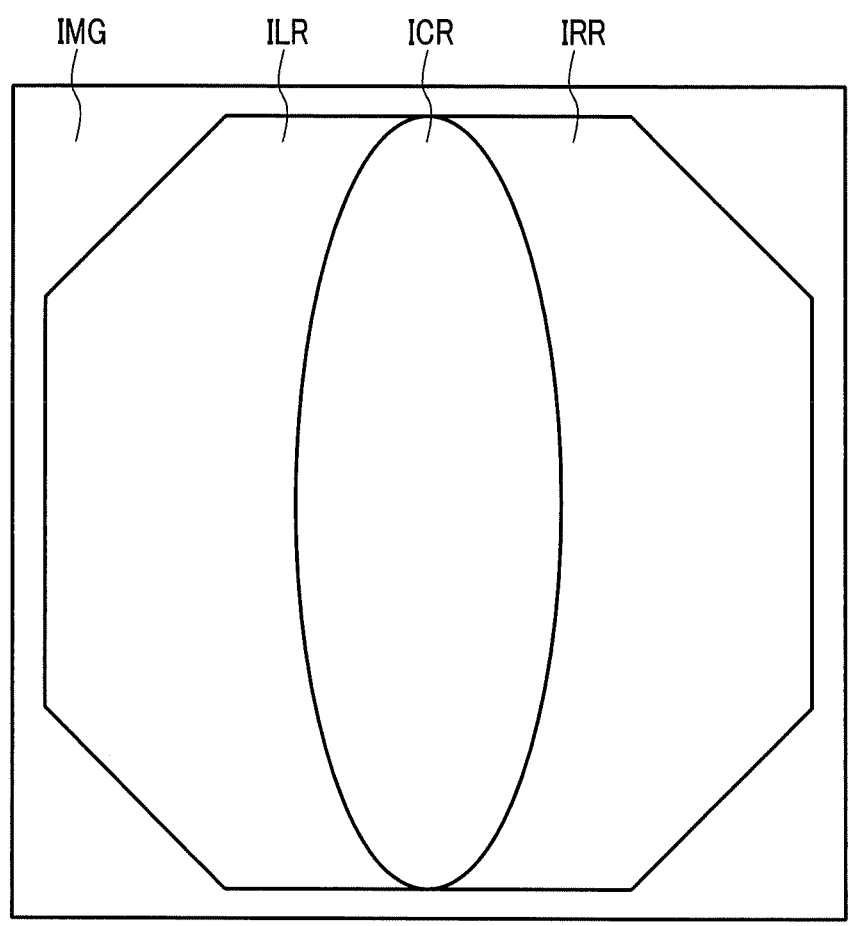
F I G. 10

IMG1

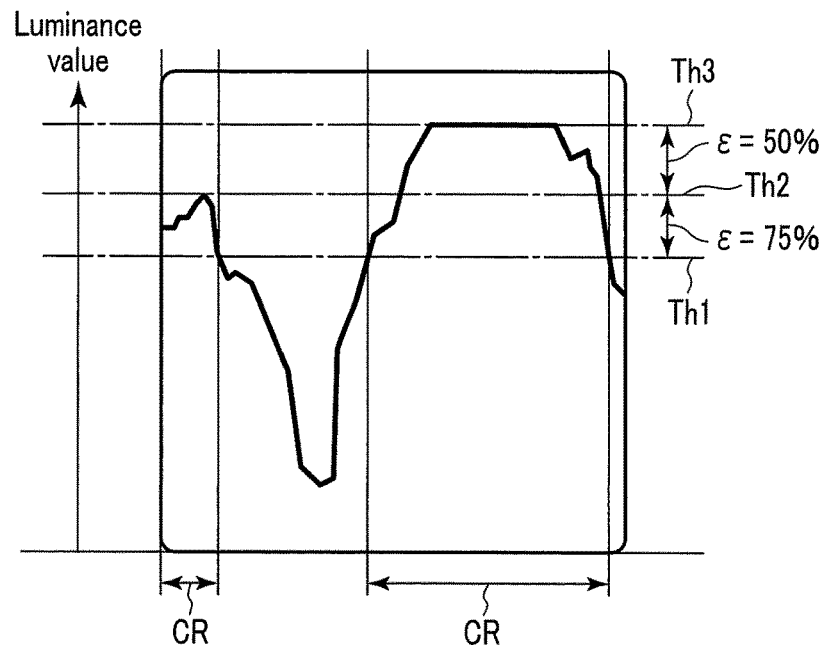
F I G. 14A
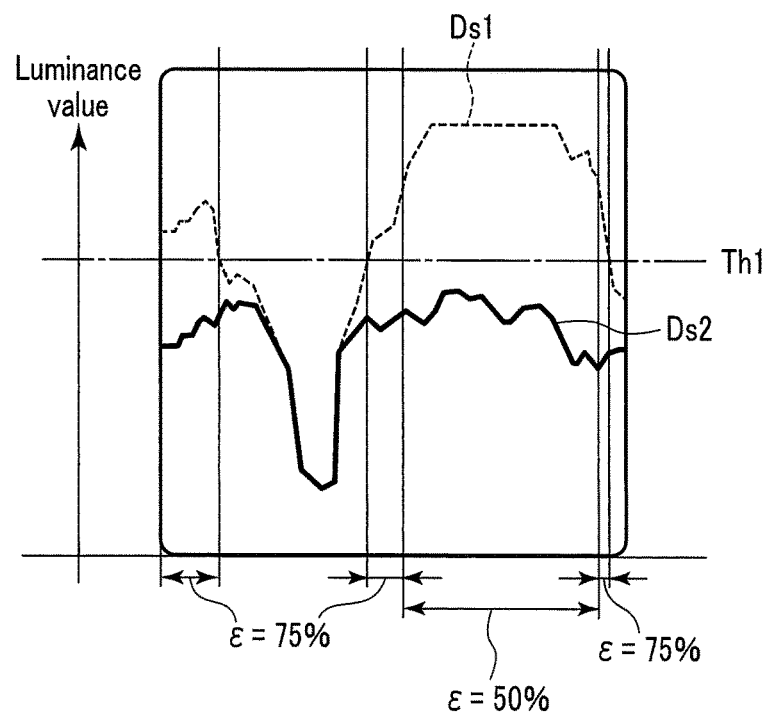
F I G. 14B

LIGHT SOURCE APPARATUS, ENDOSCOPE SYSTEM, AND ILLUMINATION CONTROL METHOD FOR ADJUSTING FIRST AND SECOND ILLUMINATION LIGHT EMITTED FROM FIRST AND SECOND ILLUMINATION LIGHT EMISSION ENDS OF A LIGHT GUIDE

CROSS-REFERENCE TO RELATED APPLICATIONS

This application is a Continuation Application of PCT Application No. PCT/JP2017/022706, filed Jun. 20, 2017, the entire contents of which are incorporated herein by reference.

BACKGROUND OF THE INVENTION

1. Field of the Invention

The present invention relates to a light source apparatus configured to radiate illumination light, an endoscope system configured to acquire an image of an observation target, and an illumination control method.

2. Description of the Related Art

Jpn. Pat. Appln. KOKAI Publication No. 2001-235686 discloses an endoscope system. The endoscope system includes a light guide, and a light modulation device configured to selectively radiate illumination light for each fiber element at an entrance end of the light guide. The light modulation device is corresponding to an entrance aperture of the fiber element, and is configured to adjust a light quantity of illumination light emitted from an exit aperture of the fiber element. Thereby, when blown-out highlights or the like exists on an endoscopic image, the drive of the light modulation device is controlled so as to suppress an illumination light quantity of a part of the blown-out highlights or the like, so that the blown-out highlights or the like can be suppressed.

BRIEF SUMMARY OF THE INVENTION

A light source apparatus includes a light source optically connectable to a scope including a light guide configured to guide light, and a first illumination light emission unit and a second illumination light emission unit configured to radiate illumination light based on the guided light on a subject. The light source is configured to emit light to be brought into the light guide. The light source apparatus also includes a light quantity distribution changing device disposed on an optical path of the light emitted from the light source. The light quantity distribution changing device is configured to control a light quantity of the light brought into each of the first illumination light emission unit and the second illumination light emission unit, so as to change a light quantity distribution of the illumination light radiated on the subject.

An endoscope system includes a scope including a light guide configured to guide light, and a first illumination light emission unit and a second illumination light emission unit configured to radiate illumination light based on the guided light, and the above mentioned light source apparatus.

An illumination control method includes: emitting light that is a basis of illumination light to a scope including a light guide configured to guide light, and a first illumination light emission unit and a second illumination light emission unit configured to radiate illumination light based on the guided light; changing a light quantity distribution of the emitted light, so as to change a light quantity distribution of the light brought into each of the first illumination light emission unit and the second illumination light emission unit; and changing a light quantity distribution of the illumination light that is generated by light emitted from each of the first illumination light emission unit and the second illumination light emission unit and radiated on a subject, by the changing of the light-quantity distribution of the light.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is an image view showing a first mirror element group that contributes to emission of illustration light from a first illumination lens, and a second mirror element group that contributes to emission of illustration light from a second illumination lens, with respect to mirror elements in a mirror element existence area corresponding to a connected scope.

FIG. 9A is an image view showing a first mirror element group and a second mirror element group that are generally grouped.

FIG. 10 shows a left region, a central region, and a right region of an image that is a basis of grouping of mirror elements.

FIG. 14A schematically shows a state in which the ratio of a first state/second state of the mirror elements is changed in accordance with a degree of blown-out highlights, in order to execute light distribution control.

FIG. 14B schematically shows a state in which a correction region that exists in a luminance distribution before correction disappears in a luminance distribution after correction by luminance correction.

DETAILED DESCRIPTION OF THE INVENTION

Hereinafter, an endoscope system according to an embodiment of the present invention will be described with reference to the accompanying drawings. In the present specification, it is assumed that the endoscope system is an endoscope system for medical use, which is used for diagnosis of a living body, or an endoscope system for industrial use, which is used for observation of the inside of tubes existing in industrial products and in various places. However, the endoscope system is not limited to such endoscope systems, and may be general devices that are inserted into the insides of observation targets and illuminate and observe the insides of the observation targets.

First Embodiment

Hereinafter, a first embodiment of the present invention will be described by taking as an example an endoscope system for medical use, in particular, a digestive endoscope for use in observation of the stomach and intestines.

[Configuration]

Figure 1:
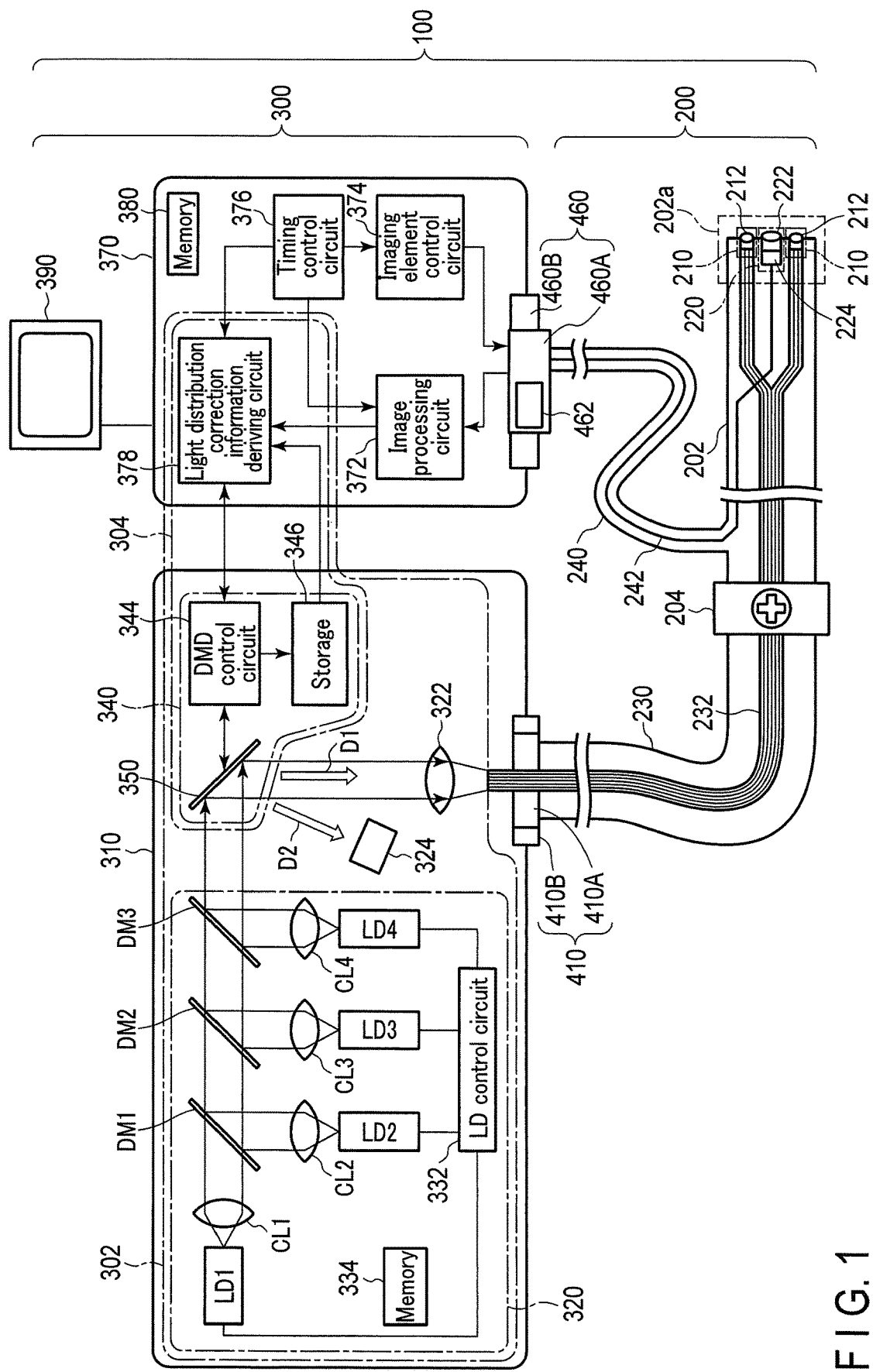
FIG. 1 is a block diagram of an endoscope system according to a first embodiment of the present invention.

FIG. 1 is a block diagram of an endoscope system 100 according to the first embodiment of the present invention. The endoscope system 100 according to the present embodiment comprises a main body 300 including an illumination light supply device 302; and a scope 200 that is detachably attached to the main body 300.

To begin with, each structural component of the endoscope system 100 according to the embodiment is described.

[Scope 200]

The scope 200 includes an elongated insertion section 202 with flexibility that can be inserted into an internal space of an observation target, for example, a body cavity or the like; and a control section 204 that is grasped by a worker such as a doctor in order to operate the insertion section 202.

The scope 200 further includes illumination light emission units 210 configured to emit illumination light toward the observation target; and an imaging unit 220 configured to acquire an image of the observation target.

Each illumination light emission unit 210 includes an illumination lens 212 for properly adjusting the spreading of illumination light.

The imaging unit 220 includes an imaging lens 222 for taking in illumination light that is reflected and scattered by the surface of the observation target; and an imaging element 224 configured to output an image signal that is information of an image formed by the imaging lens 222. For example, the imaging element 224 may comprise a photoelectric conversion element configured to convert an optical image to an electrical image signal and to output the electrical image signal.

The illumination light emission units 210 and the imaging unit 220 are disposed in a distal section 202a of the insertion section 202.

FIG. 1 illustrates, by way of example, the scope 200 including two illumination light emission units 210. However, the number of illumination light emission units 210 is not limited to two. Specifically, the scope 200 may include a greater number of illumination light emission units, or may include a single illumination light emission unit.

The scope 200 further include a light guide (LG) 232 configured to guide illumination light supplied from a light source box 310 to the illumination light emission units 210; an LG cable 230 for a connection to the light source box 310; an image signal line 242 for transmitting an image signal output from the imaging unit 220 to a camera control unit (CCU) 370; and a CCU cable 240 for a connection to the camera control unit 370.

The light guide 232 extends through the insertion section 202 and LG cable 230. The LG cable 230 is connected to the light source box 310 through an LG connector 410. The LG connector 410 comprises an LG connector portion 410A provided at an end portion of the LG cable 230 and an LG connector portion 410B provided on the light source box 310, the LG connector portion 410A and the LG connector portion 410B being detachably attached to each other.

The image signal line 242 extends through the insertion section 202 and CCU cable 240. The CCU cable 240 is connected to the camera control unit 370 through a CCU connector 460. The CCU connector 460 includes a CCU connector portion 460A provided at an end portion of the CCU cable 240 and a CCU connector portion 460B provided on the camera control unit 370, the CCU connector portion 460A and the CCU connector portion 460B being detachably attached to each other.

Figure 2:
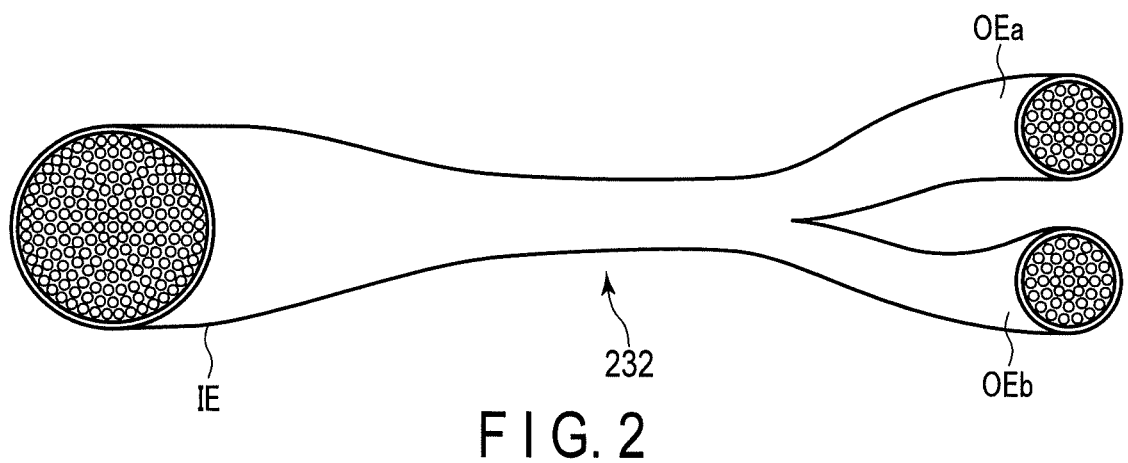
FIG. 2 is an image view of a light guide shown in FIG. 1.

FIG. 2 shows an image view of the light guide 232. The light guide 232 is a bundle fiber comprising a bundle of many optical fibers, such as several-hundred to several-thousand optical fibers. The side of the light guide 232 that is held by the LG connector portion 410A is bundled as one entrance end IE. On the other hand, the side of the light guide 232 that is opposed to the illumination lenses 212 is divided into portions, and these portions are bundled as a first exit end OEa and a second exit end OEb, respectively.

In the description below, the exit ends of the light guide 232 is denoted by reference signs OEa and OEb, for the purpose of convenience, in accordance with FIG. 2, and are expressed as "exit ends OEa and OEb". However, this does not necessarily mean that the number of the exit ends of the light guide 232 is limited to two. Specifically, the "exit ends OEa and OEb" of the light guide 232 should be differently read to mean exit ends of the light guide 232, or an exit end of the light guide 232.

Specifically, the light guide 232 includes exit ends, and the exit ends may be optically connected to illumination light emission units 210, respectively.

The entrance end IE of the light guide 232 is bundled in a substantially circular shape and is fixed so that entrance apertures of all optical fibers included in the light guide 232 are substantially flush with each other. In addition, the surface of the entrance end IE is provided with a cover glass (not shown) for protecting the entrance end IE of the light guide 232. As described above, the light guide 232 mounted in the scope 200 of the present embodiment is a 1-input/2-output branch-type bundle fiber.

Laser light as illumination light that has entered the light guide 232 from the entrance end IE is branched into two light components by the light guide 232 and emitted from the first and second exit ends OEa and OEb. The emitted light components are radiated on an observation target through the first and second illumination lenses 212 that are respectively opposed to the first and second exit ends OEa and OEb. The ratio of branching of the light quantity is, in general, substantially proportional to the ratio between the numbers of optical fibers distributed to the first and second exit ends OEa and OEb. In the present embodiment, the light quantity is distributed substantially at a ratio of 1:1.

Figure 3:
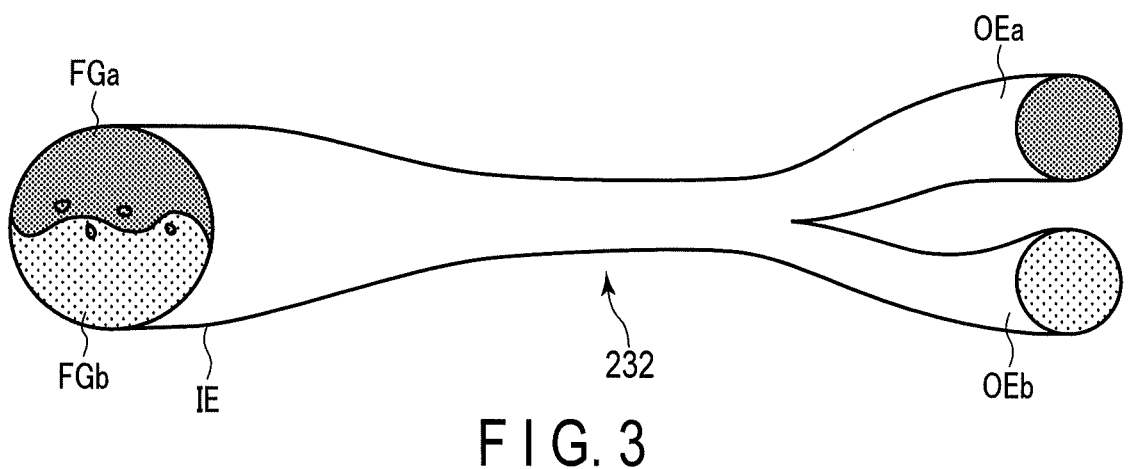
FIG. 3 is an image view showing an arrangement, at an entrance end of the light guide, of a first optical fiber group that comprises optical fibers having exit apertures at a first exit end of the light guide, and a second optical fiber group that comprises optical fibers having exit apertures at a second exit end of the light guide.

FIG. 3 is an image view showing an arrangement, at the entrance end IE of the light guide 232, of a first optical fiber group FGa that comprises optical fibers having exit apertures at the first exit end OEa of the light guide 232, and a second optical fiber group FGb that comprises optical fibers having exit apertures at the second exit end OEb of the light guide 232. As shown in FIG. 3, the entrance aperture of the first optical fiber group FGa and the entrance aperture of the second optical fiber group FGb are disposed in a generally gathered fashion, respectively. The degree of gathering depends on a fabrication process or the like of the light guide. When a light guide that utilizes a fabrication process of a general light guide is used, a substantially similar degree of gathering is normally obtained regardless of individual bodies or kinds of scopes 200.

As described above, the number of exit ends of the light guide 232 is not limited to two. Specifically, the bundle fiber constituting the light guide 232 may include optical fiber groups having exit apertures at exit ends of the light guide 232, and the optical fiber groups are optically connected to the illumination light emission units 210, respectively. In particular, in the endoscope system 100 shown in FIG. 1, the light guide 232 includes the first optical fiber group FGa and the second optical fiber group FGb, and the first optical fiber group FGa and the second optical fiber group FGb are optically connected to a first illumination light emission unit 210 and a second illumination light emission unit 210, respectively.

Referring back to FIG. 1, the imaging lens 222 and imaging element 224 provided in the distal section 202a of the insertion section 202 are combined to constitute the imaging unit 220. The imaging element 224 in this embodiment is, for example, a CMOS-type imaging element, and includes RGB color filters of a general Bayer array. Specifically, the imaging element 224 is an imaging element of a primary color filter type, and is a color imaging element configured to simultaneously acquire images of a red region, a green region and a blue region.

An image signal that is image information of an observation target, which is acquired by the imaging element 224, is transmitted to the camera control unit 370 through the image signal line 242 provided in the scope 200. The image signal line 242 extends from the imaging element 224 to the CCU connector 460, and is electrically connected to an image processing circuit 372 in the camera control unit 370 through the CCU connector 460. The image signal line 242 may be of any type, if the image signal line 242 can transmit an image signal. For example, the image signal line 242 may be composed of an electric wiring line or an optical fiber for optical communication. In FIG. 1, the image signal line 242 is depicted as being composed of a single signal line, but the image signal line 242 may be composed by arranging signal lines in parallel in accordance with the quantity of an image signal to be transmitted, or a necessary transmission speed.

Besides, in the insertion section 202 in the present embodiment, there are mounted a bending mechanism for bending the distal section 202a, a forceps hole through which a forceps or the like can be inserted, an air-feed/water-feed tube that can apply liquid or gas and can suck liquid or gas, and various functions and mechanisms mounted in a general endoscope system 100 for medical use. The depiction of these components, however, is omitted in FIG. 1 for the purpose of convenience.

Figure 4:
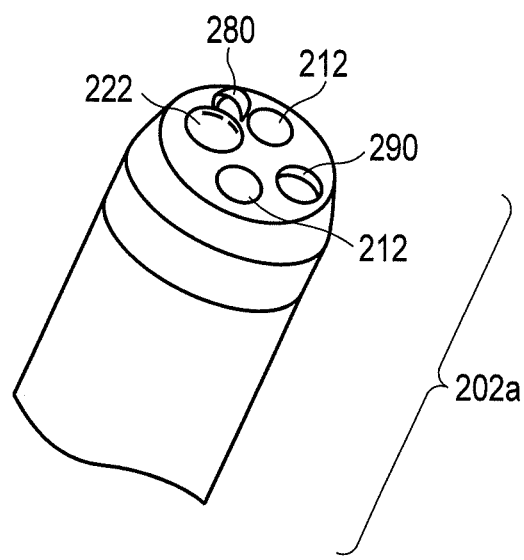
FIG. 4 shows an example of a distal section of an insertion section of a scope of an endoscope for medical use.

FIG. 4 shows an example of the distal section 202a of the insertion section 202 of the scope 200 of the endoscope 100 for medical use. In this example, the imaging lens 222 is disposed at a slightly offset position between the two illumination lenses 212. A nozzle 280 for cleaning the imaging lens 222 and a forceps channel 290 for insertion of a forceps are disposed near the imaging lens 222.

[Main Body 300]

As illustrated in FIG. 1, the main body 300 comprises the light source box 310 configured to emit illumination light; the camera control unit 370 configured to process an image signal acquired by the imaging element 224 and to output image information that is displayable; and a monitor 390 configured to display the image information, etc.

(Light Source Box 310)

The light source box 310 includes a light source unit 320 configured to emit illumination light; and a digital mirror device (DMD) unit 340 configured to adjust a light quantity distribution of illumination light emitted from the light source unit 320. The light source box 310 further includes a converging lens 322 configured to converge illumination light that is emitted from the DMD unit 340 in a direction of an arrow D1, and to bring the illumination light into the light guide 232; and a light stopper 324 configured to shut off unnecessary illumination light that is emitted from the DMD unit 340 in a direction of an arrow D2.

The light source unit 320 includes laser light sources LD1, LD2, LD3, and LD4 configured to emit beams of laser light that are illumination light; collimate lenses CL1, CL2, CL3, and CL4 configured to collimate the beams of laser light emitted from the laser light sources LD1 to LD4; three dichroic mirrors DM1, DM2, and DM3 configured to combine the collimated beams of laser light; an LD control circuit 332 configured to control the operations of the laser light sources LD1 to LD4; and a memory 334 configured to store necessary information for control.

Each of the laser light sources LD1 to LD4 is a semiconductor laser light source. The characteristics of the laser light sources LD1 to LD4 used in the present embodiment are as follows.

The laser light source LD1 emits a blue-violet laser light with a wavelength of 405 nm. An output of the laser light source LD1 is about 2 W.

The laser light source LD2 emits a blue laser light with a wavelength of 445 nm. An output of the laser light source LD2 is about 3 W.

The laser light source LD3 emits a green laser light with a wavelength of 525 nm. An output of the laser light source LD3 is about 3 W.

The laser light source LD4 emits a red laser light with a wavelength of 635 nm. An output of the laser light source LD4 is about 3 W.

The laser light sources LD1 to LD4 are electrically connected to the LD control circuit 332. The LD control circuit 332 controls the light quantities of laser light emitted from the laser light sources LD1 to LD4, and the ON/OFF of light emission of the laser light sources LD1 to LD4. The LD control circuit 332 individually controls the laser light sources LD1 to LD4 in accordance with the objective of observation, the required hue of illumination light, and the like. The LD control circuit 332 may comprise a single circuit configured to control all laser light sources LD1 to LD4, as illustrated in FIG. 1, or may comprise control circuits configured to control the respective laser light sources LD1 to LD4, and a synchronization circuit or the like configured to execute synchronization of mutual light quantities or limit emission timings.

The DMD unit 340 includes a digital mirror device 350 that is a light quantity distribution changing device disposed on an optical path of illumination light emitted from the light source unit 320; a DMD control circuit 344 configured to control the digital mirror device 350; and a DMD control information storage 346 configured to store control information of the digital mirror device 350.

The digital mirror device 350 has a function of changing the light quantity distribution of illumination light in an illumination light radiation area where illumination light is radiated, in such a manner that the light quantity distribution of illumination light emitted from the illumination light emission unit 210 becomes a desired light quantity distribution, and transmitting the illumination light to the light guide 232.

The digital mirror device 350 includes a plurality of mirror elements that are arranged two-dimensionally, and is configured to independently change the direction of a mirror surface of each mirror element. The DMD control circuit 344 executes control the mirror elements so as to switch the direction of the mirror surface of each mirror element of the digital mirror device 350.

The digital mirror device 350 will be described with reference to FIG. 5, FIG. 6A and FIG. 6B. The digital mirror device 350 is an optical device formed by a semiconductor process, and is a reflective optical device configured to control the tilt directions of mirror surfaces of many mirror elements in two states.

Figure 5:
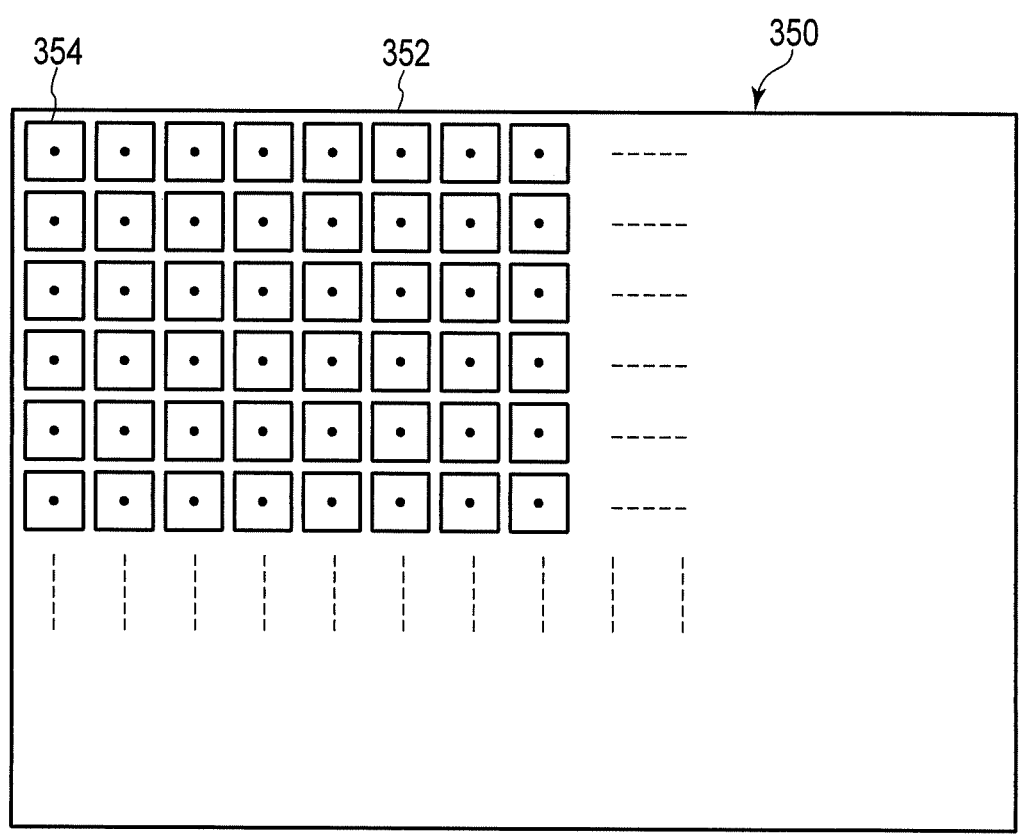
FIG. 5 shows a surface of a digital mirror device on which a mirror array is formed.

FIG. 5 shows a surface of the digital mirror device 350 on which a mirror array 352 is formed, i.e. a surface that the laser light emitted from the laser light sources LD1 to LD4 reaches. In the digital mirror device 350, several-hundred mirror elements 354 are arranged in a matrix in vertical and horizontal directions, thus forming the mirror array 352.

Figure 6A:
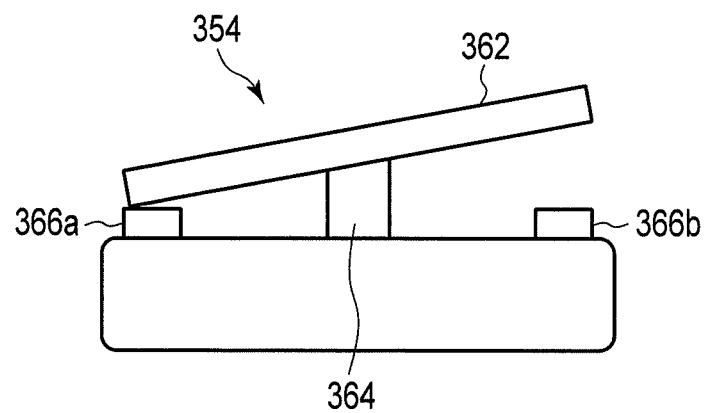
FIG. 6A is an image view of a cross-sectional configuration schematically showing a basic operation of a mirror element shown in FIG. 5.
Figure 6B:
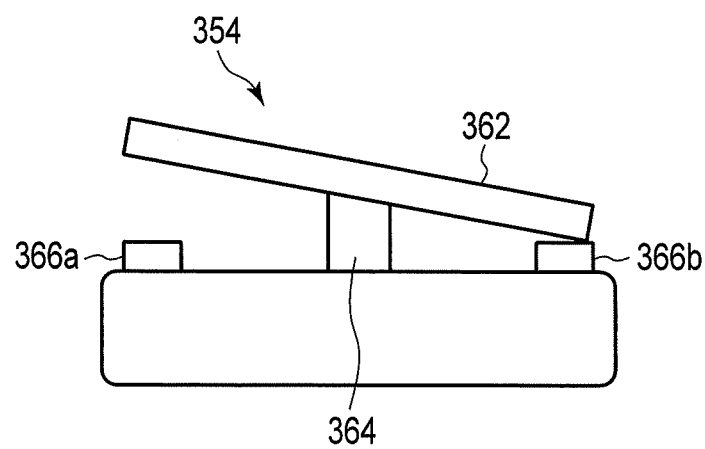
FIG. 6B is an image view of a cross-sectional configuration schematically showing a basic operation of a mirror element shown in FIG. 5, the mirror element being in a state different from the state of the mirror element shown in FIG. 6A.

FIG. 6A and FIG. 6B are image views of cross-sectional configurations schematically showing a basic operation of a mirror element 354. FIG. 6A and FIG. 6B show the mirror element 354 in mutually different states.

The mirror element 354 includes a mirror 362, a hinge 364 supporting the mirror 362 tiltably, and two electrodes 366a and 366b provided to face the mirror 362.

If such a control signal as to generate attractive force between the electrode 366a and mirror 362 is applied, the hinge 364 is deformed by the generated attractive force, so that the mirror 362 tilts, as shown in FIG. 6A, and an end portion of the mirror 362 comes in contact with the electrode 366a and stops. It is assumed that this state is a first state.

Conversely, if such a control signal as to generate attractive force between the electrode 366b and mirror 362 is applied, the hinge 364 is deformed in the opposite direction by the generated attractive force, so that the mirror 362 tilts in the opposite direction, as shown in FIG. 6B, and an end portion of the mirror 362 comes in contact with the electrode 366b and stops. It is assumed that this state is a second state.

In the first state, the mirror 362 tilts by approximately +10° and stops. In the second state, the mirror 362 tilts by approximately −10° and stops. The digital mirror device 350 can execute control so that each mirror element 354 is set in either the first state or the second state.

As the digital mirror device 350, a digital mirror device including tens of thousands to several millions of mirror elements 354 is commercially available. In the present embodiment, use is made of the digital mirror device 350 in which the number of mirror elements 354 is greater than the number of entrance apertures of the optical fibers at the entrance end IE of the light guide 232. As shown in FIG. 5, in the digital mirror device 350, the mirror elements 354 are arranged in a matrix. On the other hand, as shown in FIG. 2, the entrance apertures of the optical fibers at the entrance end IE of the light guide 232 are not arranged in a matrix but are bundled at random. Thus, the mirror elements 354 and the entrance apertures of the optical fibers are not in a one-to-one correspondence. However, the number of mirror elements 354 is sufficiently large, and, as shown in FIG. 3, the entrance apertures of optical fibers connected to the first exit end OEa and second exit end OEb are generally collectively arranged.

(Camera Control Unit 370)

The camera control unit 370 is connected to the scope 200 through the CCU connector 460. In addition, the camera control unit 370 is further connected to the light source box 310 and the monitor 390 through electrical wiring lines.

FIG. 1 depicts the camera control unit 370 as a single unit. Alternatively, the camera control unit 370 may comprise units. In this case, the units cooperatively execute a process. Besides, the units may be configured to cooperatively execute a process through a network.

The camera control unit 370 includes an image processing circuit 372 configured to process an image signal that is acquired by the imaging element 224 and is transmitted through the image signal line 242; and an imaging element control circuit 374 configured to control the operation of the imaging element 224. The imaging element control circuit 374 and image processing circuit 372 are connected to a common timing control circuit 376, and operate by using timing signals from the timing control circuit 376 as triggers.

The camera control unit 370 further includes a light distribution correction information deriving circuit 378 configured to derive light distribution correction information, based on image information processed by and output from the image processing circuit 372, and DMD control information from the DMD control circuit 344 included in the light source box 310. The light distribution correction information deriving circuit 378 also operates, based on a timing signal from the timing control circuit 376. Thereby, it becomes possible to correlate the image captured by the imaging element 224, the DMD control information representative of the state of the mirror array 352 of the digital mirror device 350 at that time, and the light distribution correction information representative of the state of the mirror array 352 at a time of the next imaging.

The light distribution correction information deriving circuit 378 constitutes, in cooperation with the light source box 310, the illumination light supply device 302 configured to control the light distribution of illumination light and to supply the illumination light to the light guide 232 mounted in the scope 200. In other words, the light distribution correction information deriving circuit 378 constitutes, in cooperation with the DMD unit 340, a light distribution control device 304 configured to control the light distribution of illumination light output from the light source unit 320.

(Monitor 390)

The monitor 390 displays to a worker an image captured by the imaging element 224, and necessary information for endoscopic observation.

[Operation]

Next, a basic operation of the endoscope system 100 according to the present embodiment will be described.

If the endoscope system 100 is powered on, electric power is successively supplied to respective circuits and devices, like an ordinary endoscope. In the light source box 310, the LD control circuit 332 starts the operation, and predetermined currents are supplied to the laser light sources LD1 to LD4. The LG connector portion 410B includes a shutter (not shown) configured to prevent laser light from leaking to the outside when the scope 200 is not connected.

Next, a worker connects the LG connector portion 410A included in the scope 200 to the LG connector portion 410B of the light source box 310, and connects the CCU connector portion 460A to the CCU connector portion 460B of the camera control unit 370. The CCU connector portion 460A included in the scope 200 is provided with a memory 462 configured to store information relating to the kind and individual body of the scope 200. The camera control unit 370 reads out necessary information relating to the connected scope 200 from the memory 462.

The memory 462 may store, in addition to the information relating to the kind and individual body of the scope 200, information relating to the light guide 232 that is mounted, i.e. the number of optical fibers, the shape of the entrance end IE, the number of exit ends OEa, OEb, and the ratio between the numbers of optical fibers of the exit ends OEa, OEb. In addition, the memory 462 may store information relating to the size and light reception sensitivity of the imaging element 224 included in the scope 200, and wavelength characteristics of color filters. Further, the memory 462 may store optical fiber group entrance end/exit end distribution information that is arrangement information at the entrance end IE of optical fibers having exit apertures at two exit ends OEa and OEb of the light guide 232, as shown in FIG. 3, and DMD control information that is information of the arrangement relationship between the mirror elements 354 of the digital mirror device 350 and the exit ends OEa and OEb of the light guide 232.

In the case where the memory 462 included in the CCU connector 460 stores the DMD control information, when the scope 200 is connected to the main body 300, the DMD control information is transmitted to the DMD control information storage 346 in the DMD unit 340 by an electrical wiring line (not shown).

Note that the information stored in the memory 264 included in the scope 200 may be at least identification (ID) information that enables distinction of the individual body of the scope 200. In this case, the above-described various pieces of information may be stored in a memory 380 included in the camera control unit 370 by being correlated with the ID information of the scope 200. Besides, such a configuration may be adopted that the above-described various pieces of information are acquired from the outside through the Internet, an infrastructure in a hospital, a cloud, etc.

If the connection of the scope 200 is confirmed, the LD control circuit 332 provided in the light source box 310 turns on at least one of the laser light sources LD1 to LD4 with such a light quantity as to enable observation. At this time, which of the laser light sources LD1 to LD4 is to be turned on can be properly set in accordance with the objective of observation or an observation target. Normally, all the laser light sources LD1 to LD4 are turned on so as to emit white illumination light. The ratio between light quantities of the laser light sources LD1 to LD4 at a time when white light is emitted is prestored in the memory 334 provided in the light source box 310.

The timing control circuit 376 included in the camera control unit 370 and the LD control circuit 332 are connected by an electrical wiring line (not shown), and the LD control circuit 332 causes the laser light sources LD1 to LD4 to emit light in accordance with a timing signal from the timing control circuit 376. The laser light sources LD1 to LD4 emit laser light of intrinsic wavelengths of the laser light sources in accordance with driving currents supplied from the LD control circuit 332. The laser light sources LD1 to LD4 have temperatures controlled at desired values by a laser temperature stabilizing unit (not shown), for example, a Peltier element. Thereby, a variation of laser wavelength or a variation of driving current due to environmental temperatures can be suppressed, and the laser light sources LD1 to LD4 can stably emit light.

The beams of laser light emitted from the laser light sources LD1 to LD4 are converted into parallel beams by the collimate lenses CL1 to CL4 provided near laser light emission portions of the laser light sources LD1 to LD4, and travel.

As shown in FIG. 1, the dichroic mirrors DM1 to DM3 are disposed on optical paths of laser light.

The dichroic mirror DM1 is a dichroic mirror configured to transmit light of a wavelength of 405 nm emitted from the laser light source LD1, and to reflect light of a wavelength of 445 nm emitted from the laser light source LD2. The dichroic mirror DM2 is a dichroic mirror configured to transmit the light of the wavelength of 405 nm emitted from the laser light source LD1 and the light of the wavelength of 445 nm emitted from the laser light source LD2, and to reflect light of a wavelength of 525 nm emitted from the laser light source LD3. The dichroic mirror DM3 is a dichroic mirror configured to transmit the light of the wavelength of 405 nm emitted from the laser light source LD1, the light of the wavelength of 445 nm emitted from the laser light source LD2, and the light of the wavelength of 525 nm emitted from the laser light source LD3, and to reflect light of a wavelength of 635 nm emitted from the laser light source LD4.

The laser light of the wavelength of 405 nm emitted from the laser light source LD1 is transmitted through the dichroic mirrors DM1, DM2, and DM3, and reaches the digital mirror device 350.

The laser light of the wavelength of 445 nm emitted from the laser light source LD2 is reflected by the dichroic mirror DM1 and the direction of travel is deflected by approximately 90°. Then, the laser light travels toward the dichroic mirror DM2, is transmitted through the dichroic mirrors DM2 and DM3, and reaches the digital mirror device 350.

The laser light of the wavelength of 525 nm emitted from the laser light source LD3 is reflected by the dichroic mirror DM2 and the direction of travel is deflected by approximately 90°. Then, the laser light travels toward the dichroic mirror DM3, is transmitted through the dichroic mirror DM3, and reaches the digital mirror device 350.

The laser light of the wavelength of 635 nm emitted from the laser light source LD4 is reflected by the dichroic mirror DM3 and the direction of travel is deflected by approximately 90°. Then, the laser light travels toward the digital mirror device 350, and reaches the digital mirror device 350.

As described above, the laser light emitted from the laser light sources LD1 to LD4 are combined and mixed into one optical path, and the combined and mixed laser light reaches the digital mirror device 350.

The laser light that has reached the digital mirror device 350 is selectively reflected in two travel directions by the mirror elements 354 on the mirror array 352 of the digital mirror device 350. As described above, the mirror element 354 is in one of the first state and second state in which the directions of reflection are different.

In the first state, the mirror element 354 brings the reaching illumination light into the light guide 232. In the second state, the mirror element 354 diverts the reaching illumination light from the light guide 232, or, in other words, brings the reaching illumination light in a direction other than the direction toward the light guide 232.

The laser light reflected by the mirror element 354 in the first state travels in a first reflection direction D1, passes through the converging lens 322, and enters the entrance end IE of the light guide 232 of the scope 200, which is connected to the LG connector 410.

On the other hand, the laser light reflected by the mirror element 354 in the second state travels in a second reflection direction D2 and reaches the light stopper 324. The light stopper 324 has a function of absorbing the laser light and converting the laser light to heat. Most of the laser light that has reached the light stopper 324 is absorbed by the light stopper 324 and converted to heat. Thereby, it is possible to prevent an unused laser light from leaking to the outside of the light source box 310, and to prevent an unused laser light from being radiated on a member within the light source box 310, and the safety is enhanced.

The laser light that travels in the first reflection direction D1 and enters the entrance end IE of the light guide 232 of the scope 200 is guided to the distal section 202a of the insertion section 202 by the light guide 232 mounted in the scope 200. As described above, the light guide 232 comprises a 2-branch type bundle fiber including one entrance end IE and two exit ends OEa and OEb. As regards the laser light that has entered the entrance end IE of the light guide 232, the ratio between light quantities emitted from the two exit ends OEa and OEb is determined by the state (the distribution of dispositions of the first state and second state is called "state") of the mirror elements 354 included in the digital mirror device 350, and by the ratio of branching of optical fibers at the exit ends OEa and OEb of the light guide 232. Laser light emitted from the two exit ends OEa and OEb of the light guide 232 is radiated on an observation target through the illumination lenses 212.

The illumination light emitted from the two illumination lenses 212 is reflected or scattered on the surface or in the inside of the observation target. Part of the reflected/scattered light (a general term of reflected light and scattered light) reaches the imaging element 224 through the imaging lens 222. Specifically, the imaging element 224 captures an image of the observation target illuminated by the illumination light emitted from the illumination lenses 212. The image captured by the imaging element 224 is converted to an electric signal by the imaging element 224 and is transmitted to the image processing circuit 372 of the camera control unit 370 through the image signal line 242 provided in the scope 200.

The image processing circuit 372 receives the image signal transmitted by the image signal line 242, performs proper image processing on the image signal, creates image information that is displayable, and transmits the image information to the monitor 390. The monitor 390 displays the received image information.

[Light Distribution Control]

Next, an operation of light distribution control of illumination light emitted from the distal end of the insertion section 202 will be described.

The digital mirror device 350 controls the light quantities of illumination light that exits the exit ends OEa and OEb of the light guide 232, and the light quantity ratio, i.e. the light distribution, of illumination light emitted from the first exit end OEa and second exit end OEb of the light guide 232. As described above, when the mirror element 354 of the digital mirror device 350 is in the first state, the illumination light enters the light guide 232 provided in the scope 200 and exits the exit end OEa, OEb of the light guide 232. On the other hand, when the mirror element 354 of the digital mirror device 350 is in the second state, the illumination light reaches the light stopper 324 and is not emitted to the outside of the light source box 310.

For example, when the light quantity of the laser light emitted from the second exit end OEb is to be set at 50% of the light quantity of the laser light emitted from the first exit end OEa, this is achieved by setting in the first state all mirror elements 354 of the digital mirror device 350 that correspond to the entrance apertures of the light guide 232 connected to the first exit end OEa, and by temporally or spatially setting in the first state half of the mirror elements 354 of the digital mirror device 350 that correspond to the LD entrance apertures connected to the second exit end OEb, and setting the other half in the second state.

A description is given of the case of temporally setting the first state for one half and temporally setting the second state for the other half. Such control is executed that, compared to the time in which the mirror elements 354 of the digital mirror device 350 that correspond to the entrance apertures of the light guide 232 connected to the first exit end OEa are in the first state, the mirror elements 354 of the digital mirror device 350 that correspond to the entrance apertures of the light guide 232 connected to the second exit end OEb are set in the first state during half of this time and are set in the second state during the other half of the time.

For example, during an imaging period of one frame of the imaging element 224, when the mirror elements 354 of the digital mirror device 350 that correspond to the entrance apertures of the light guide 232 connected to the first exit end OEa are set in the first state during the entire one-frame period, the mirror elements 354 of the digital mirror device 350 that correspond to the entrance apertures of the light guide 232 connected to the second exit end OEb are set in the first state during half of the one-frame period and are set in the second state during the other half of the one-frame period. Thereby, the above can be achieved.

A description is given of the case of spatially setting the first state for one half and spatially setting the second state for the other half. This can be achieved by setting, when all mirror elements 354 of the digital mirror device 350 that correspond to the entrance apertures of the light guide 232 connected to the first exit end OEa are set in the first state, half of the mirror elements 354 of the digital mirror device 350 that correspond to the entrance apertures of the light guide 232 connected to the second exit end OEb are set in the first state, and the other half are set in the second state.

In the example of the spatial setting, it is preferable that the mirror elements 354 that are set in the first state and the mirror elements 354 that are set in the second state are two-dimensionally alternately arranged, for example, like a checkerboard pattern. Thereby, illumination light is emitted with a substantially uniform light quantity distribution from the exit surface of the second exit end OEb, the light quantity of the illumination light being about half the light quantity of the first exit end OEa.

It is also preferable that two methods are combined for the control of the light quantity ratio. For example, when the difference in light quantity is large, for example, like 100:1, stable control can be achieved by combining, for example, 1/10 in the spatial setting and 1/10 in the temporal setting.

Next, a concrete method of light distribution control by the digital mirror device 350 will be described. Methods of light distribution control by the digital mirror device 350 are generally classified into two kinds of methods. Specifically, there are (A) an advance memory method that is a method in which the correlation between the state of the mirror element group of the digital mirror device 350 and the light distribution of illumination light emitted from the distal end of the insertion section 202 at that time is prestored, and control is executed based on the correlation, and (B) a feedback method in which when the state of the mirror element group of the digital mirror device 350 is changed, the variation of the luminance distribution of an image is confirmed, and the state of the mirror elements 354 of the digital mirror device 350 is corrected by utilizing the information of the variation, thereby performing adjustment to obtain a proper light distribution.

In the present embodiment, an example of the case of using the (A) advance memory method is illustrated.

(A) "Advance Memory Method"

In this method, the main body 300 and scope 200 of the endoscope system 100 are combined and, while the state of the mirror element 354 included in the digital mirror device 350 is being varied, it is confirmed from which of the first exit end OEa and second exit end OEb the light reflected by the mirror element 354 is emitted, and the related information is stored in the memory included in the endoscope system 100. In the present embodiment, it is assumed that the related information is stored in the memory 462 mounted in the CCU connector 460 of the scope 200. In addition, it is assumed that when the scope 200 is connected to the main body 300, this information is transmitted to the DMD control information storage 346 in the light source box 310 of the main body 300 by an electrical wiring line (not shown).

Figure 7:
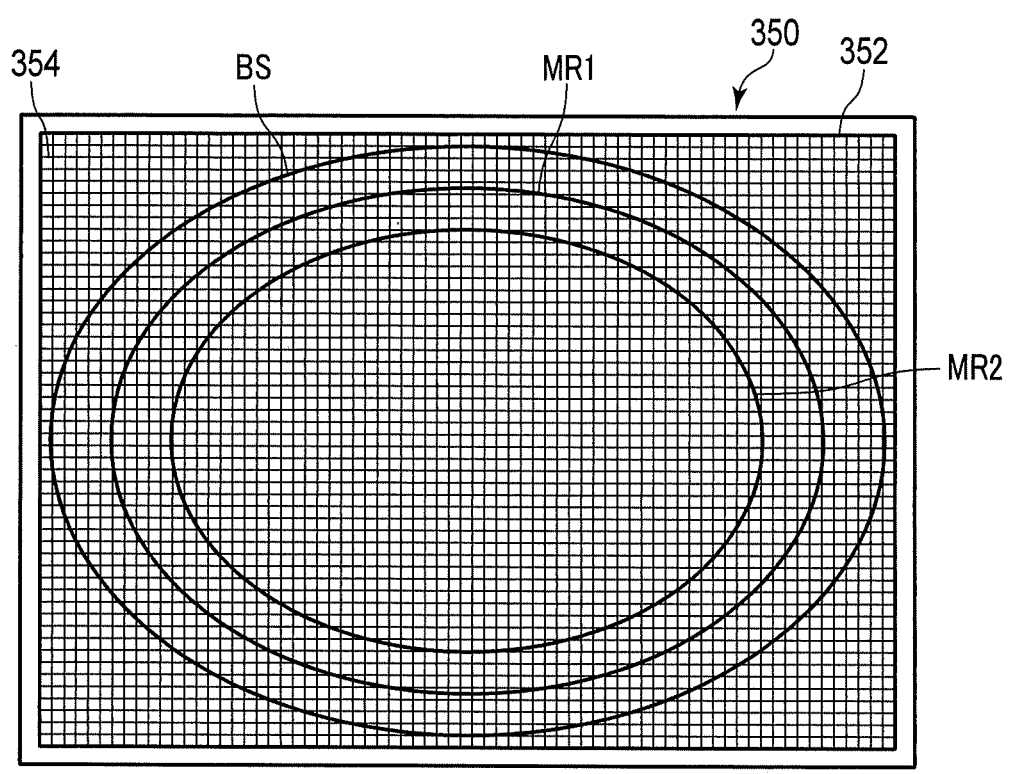
FIG. 7 shows three beam spots formed on the mirror array of the digital mirror device.

An illumination light radiation area, i.e. a beam spot, which is an area where laser light emitted from the laser light sources LD1 to LD4 is radiated on the mirror element group included in the digital mirror device 350, has an oval shape, as shown in FIG. 7. The reason for this is that, since the laser light sources LD1 to LD4 are semiconductor lasers, the beam of laser light emitted from the laser light sources LD1 to LD4 has an oval beam spot, and that the mirror surface of the digital mirror device 350 is inclined to the optical path of the laser light.

FIG. 7 shows three beam spots formed on the mirror array 352 of the digital mirror device 350. An outermost beam spot BS is an area where laser light that is emitted from the laser light sources LD1 to LD4 and travels through the dichroic mirrors DM1 to DM3 may possibly be radiated. In consideration of designs, individual characteristics of lasers and fabrication variances, the beam spot BS is set as a largest area. In other words, no laser light is radiated on mirror elements 354 existing outside the beam spot BS. Thus, in this embodiment, all mirror elements 354 outside the beam spot BS are set in the second state, and stray light or the like, such as scattered light of laser light or outside light in the light source box 310, is prevented from being radiated on the vicinity of the entrance end IE of the light guide 232.

A beam spot in the inside of the beam spot BS is an effective mirror element existence area MR1, i.e. an area that surrounds mirror elements 354 that reflect light toward the entrance end IE of the light guide 232 in the first state when a scope having an entrance area of a largest light guide 232 is connected. Even when there occur fabrication variances or a positional displacement at a time of connection, in order to bring sufficient illumination light into the entrance area of the light guide 232, the effective mirror element existence area MR1 is set to be narrower than the beam spot BS.

A further inner beam spot is a mirror element existence area MR2 that is an area that surrounds mirror elements 354 that reflect laser light toward the entrance aperture of the light guide 232 of the scope 200 used in the present embodiment. The mirror element existence area MR2 varies in accordance with the scope 200 that is connected.

The illumination light radiation area refers to an area of the mirror elements 354 of the digital mirror device 350 on which illumination light is radiated. Accordingly, when the scope 200 is not connected, the illumination light radiation area means the beam spot BS. However, when the scope 200 is connected, although laser light is radiated on an area that is within the beam spot BS and outside the mirror element existence area MR2 corresponding to the connected scope 200, this laser light is not emitted from the distal end of the insertion section 202. Thus, the illumination light radiation area in the case where the scope 200 is connected refers to the mirror element existence area MR2 corresponding to the connected scope 200 as an effective illumination light radiation area.

Figure 8A:
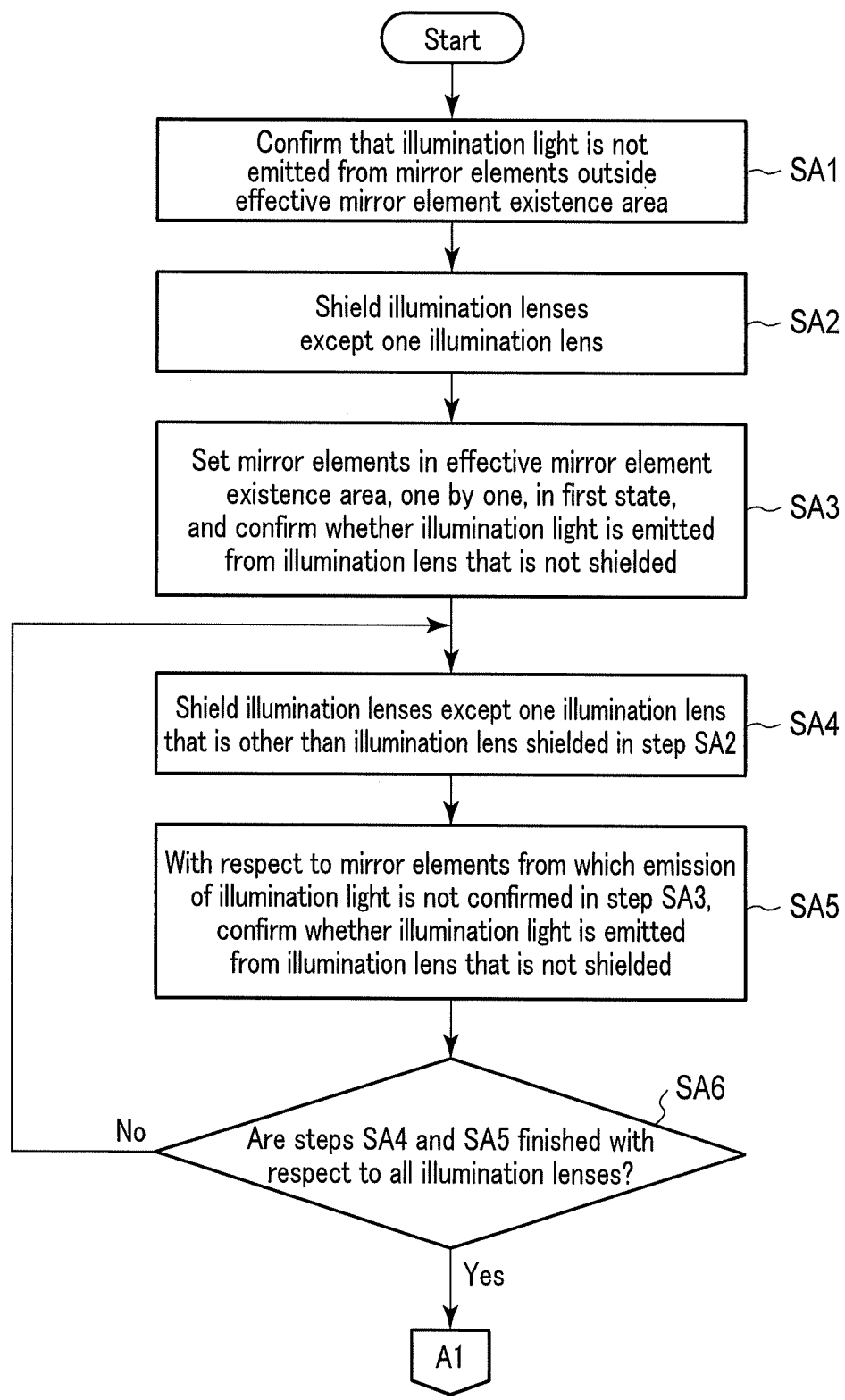
FIG. 8A shows a first half of a flowchart illustrating a procedure of light distribution control by an advance memory method.
Figure 8B:
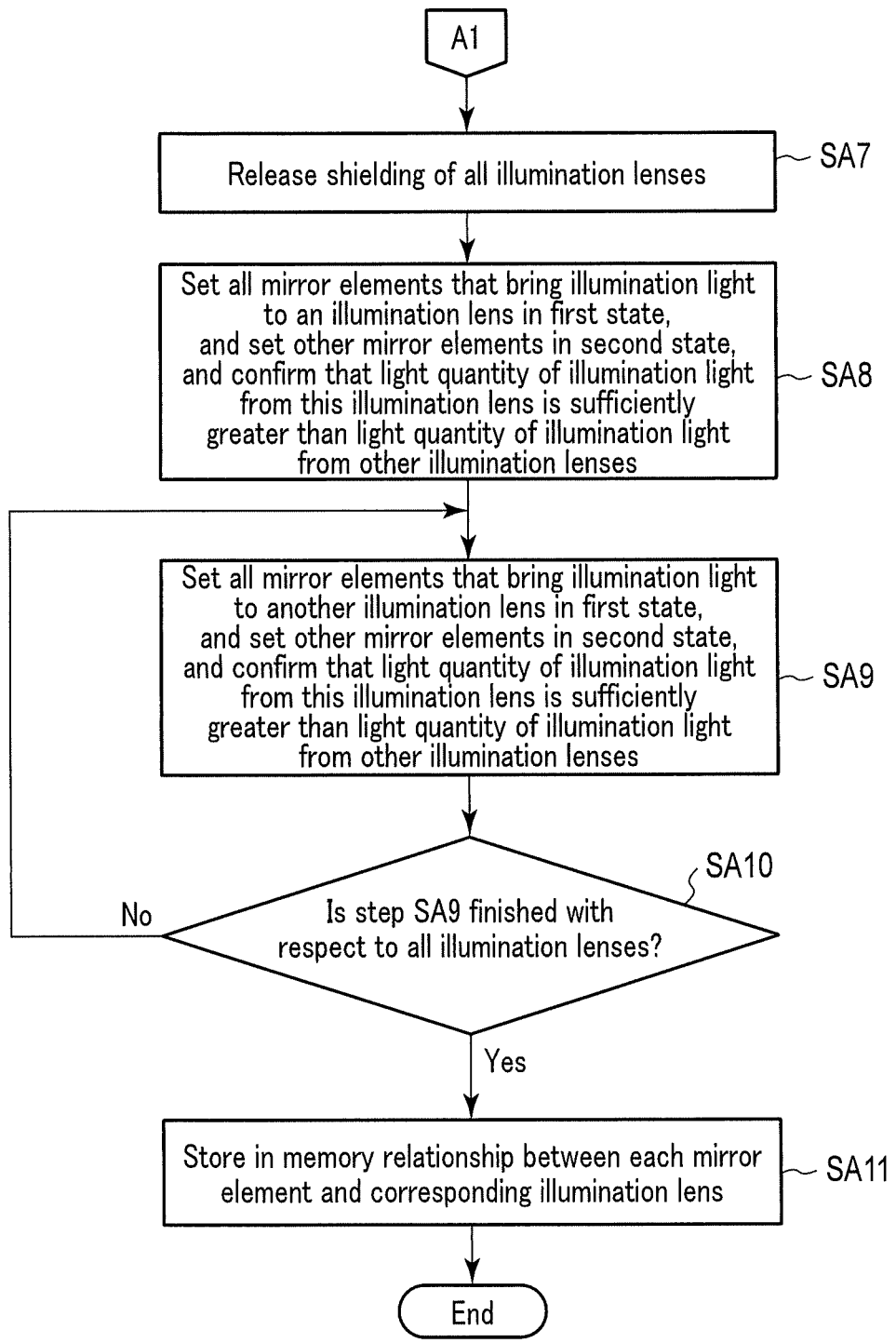
FIG. 8B shows a second half of the flowchart illustrating the procedure of the light distribution control by the advance memory method.

Next, a procedure of advance memory by the (A) advance memory method will be described with reference to FIG. 8A and FIG. 8B. Here, a description is given of a procedure of examining whether illumination light is emitted from the first exit end OEa, whether illumination light is emitted from the second exit end OEb, or whether illumination light is emitted from neither the first exit end OEa nor the second exit end OEb, when each of the mirror elements 354 is set in the first state on a one-by-one basis and all the other mirror elements 354 are set in the second state, and storing an examination result in the memory.

(Step SA1: Confirmation of Non-Emission of Illumination Light)

All mirror elements 354 located in the inside of the effective mirror element existence area MR1 are set in the second state, and all mirror elements 354 located inside the beam spot BS and outside the effective mirror element existence area MR1 are set in the first state. At this time, it is confirmed that there is no change in the image captured by the imaging element 224, i.e. no illumination light is emitted. At this time, it is preferable to dispose, within the view angle of the imaging unit 220, a scattering plate, or a fluorescent plate configured to emit fluorescence by laser light. Thereby, it becomes easier to confirm whether illumination light is emitted or not.

If illumination light is emitted, it is confirmed whether an LG post is correctly inserted in the LG connector 410, or whether there is no abnormality in the mirror array 352 of the digital mirror device 350, the converging lens 322, etc. Then, step SA1 is executed once again.

(Step SA2: Shielding of Illumination Lens 212)

Next, illumination lenses at the distal end of the scope 200, excluding one illumination lens, are shielded. For example, one of the two illumination lenses 212 is shielded. The shielding can be performed by a dedicated cover or the like. At this time, the other illumination lens 212 and the imaging lens 222 are not shielded. Here, the description is given on the assumption that a second illumination lens 212 is shielded and a first illumination lens 212 is opened.

(Step SA3: Confirmation of Emission of Illumination Light with Respect to Each Mirror Element 354)

The mirror elements 354 in the inside of the effective mirror element existence area MR1 are successively set in the first state one by one, and it is confirmed whether or not the image captured by the imaging element 224 is brightened, i.e. whether illumination light is emitted from the first illumination lens 212. This confirmation is performed for all mirror elements 354 within the effective mirror element existence area MR1. Then, the confirmation result is stored in the memory 462.

(Step SA4: Change of Illumination Lens to be Shielded)

Next, the illumination lenses excluding one illumination lens that is other than the illumination lens shielded in step SA2 are shielded. For example, the first illumination lens 212, which is the illumination lens 212 on the opposite side to the second illumination lens 212 shielded in step SA2, is shielded. Like step SA2, the shielding is performed by a dedicated cover or the like.

(Step SA5: Confirmation of Emission of Illumination Light with Respect to Mirror Elements 354 from which Emission of Illumination Light is not Confirmed)

Among the mirror elements 354 in the effective mirror element existence area MR1, as regards the mirror elements 354 excluding the mirror elements 354 from which the emission of illumination light from the first illumination lens 212 that is not shielded has been confirmed in the test of step SA3, i.e. with respect to the mirror elements 354 from which the emission of illumination light has not been confirmed in step SA3, it is confirmed like step SA3 whether illumination light is emitted from the second illumination lens that is not shielded. Then, the confirmation result is stored in the memory 462. In the present embodiment, for the purpose of simplicity, the method of using the result of step SA3 is adopted. However, it is also preferable to perform, like step SA3, the confirmation with respect to all mirror elements 354 once again.

(Step SA6: Determination of the End of Confirmation of Emission of Illumination Light)

It is determined whether steps SA4 and SA5 are finished for all illumination lenses 212. In the case of "No", steps SA4 and SA5 are repeated for the remaining illumination lenses 212, and the shielding and the confirmation of emission of illumination light are performed. In the case of "Yes", the next step SA7 is performed.

(Step SA7: Opening of all Illumination Lenses 212)

The shielding of all illumination lenses 212 is released. For example, following the shielding of the first illumination lens 212 and the confirmation of emission of illumination light with respect to the second illumination lens 212, the shielding of the first illumination lens 212 is released. Specifically, the dedicated cover or the like is removed.

(Step SA8: Confirmation of Light Quantity of Illumination Light from One Certain Illumination Lens 212)

All mirror elements 354 that bring illumination light to one certain illumination lens 212 are set in the first state, and the other mirror elements 354 are set in the second state, and it is confirmed that the light quantity of illumination light from this illumination lens 212 is sufficiently greater than the light quantity of illumination light from other illumination lenses 212. For example, all mirror elements 354 with respect to which the emission of illumination light from the first illumination lens 212 has been confirmed in step SA3 are set in the first state, and the other mirror elements 354 are set in the second state, and it is confirmed that illumination light is substantially emitted from only the first illumination lens 212, or that the illumination light emitted from the first illumination lens 212 is sufficiently greater than the illumination light emitted from the second illumination lens 212.

(Step SA9: Confirmation of Light Quantity of Illumination Light from Another Illumination Lens 212)

All mirror elements 354 that bring illumination light to another illumination lens 212 are set in the first state, and the other mirror elements 354 are set in the second state, and it is confirmed that the light quantity of illumination light from this illumination lens 212 is sufficiently greater than the light quantity of illumination light from other illumination lenses 212. For example, all mirror elements 354 with respect to which the emission of illumination light from the second illumination lens 212 has been confirmed in step SA5 are set in the first state, and the other mirror elements 354 are set in the second state, and it is confirmed that illumination light is substantially emitted from only the second illumination lens 212, or that the illumination light emitted from the second illumination lens 212 is sufficiently greater than the illumination light emitted from the first illumination lens 212.

(Step SA10: Determination of the End of Confirmation of Light Quantity of Illumination Light)

It is determined whether step SA9 is finished for all illumination lenses 212. In the case of "No", step SA9 is repeated for the remaining illumination lenses 212, and the confirmation of the light quantity of illumination light is performed. In the case of "Yes", the next step SA11 is performed.

(Step SA11: Memory of Correspondence Relation Between Mirror Elements 354 and Illumination Lenses 212)

The relationship between each of the mirror elements 354 and the corresponding illumination lens 212 is stored in the memory 462.

By the above steps, the mirror elements 354 that contribute to the emission of illumination light from each of the illumination lenses 212 can be grouped. For example, the mirror elements 354 that contribute to the emission of illumination light from the first illumination lens 212, and the mirror elements 354 that contribute to the emission of illumination light from the second illumination lens 212 can be grouped. FIG. 9 shows an example of the result of grouping.

FIG. 9 is an image view showing a first mirror element group 354Ga that is mirror elements 354 that contribute to emission of illustration light from the first illumination lens 212, and a second mirror element group 354Gb that is mirror elements 354 that contribute to emission of illustration light from the second illumination lens 212, with respect to the mirror elements 354 in the mirror element existence area MR2 (FIG. 7) on the mirror array 352 of the digital mirror device 350 corresponding to the connected scope 200. Here, the mirror element existence area MR2 corresponding to the connected scope 200 is divided into two illumination light selection areas MR2a and MR2b. Specifically, the illumination light selection area in which the first mirror element group 354Ga exists is referred to as "first illumination light selection area MR2a", and the illumination light selection area in which the second mirror element group 354Gb exists is referred to as "second illumination light selection area MR2b". In the present embodiment, such a configuration is adopted that the illumination light radiation area is divided into two illumination light selection areas MR2a and MR2b.

The first mirror element group 354Ga and second mirror element group 354Gb, which are divided as described above, are controlled by the DMD control circuit 344. Specifically, the DMD control circuit 344 controls, separately, the state of the first mirror element group 354Ga and the state of the second mirror element group 354Gb.

Here, the description has been given of the example in which the illumination light radiation area is divided into the two illumination light selection areas MR2a and MR2b. Needless to say, in a configuration in which the scope 200 includes a greater number of illumination light emission units 210, the illumination light radiation area is divided into the same number of illumination light selection areas as the number of illumination light emission units 210.

Although FIG. 9 shows the example in which the illumination light radiation area is finely divided into the two illumination light selection areas, based on the (A) advance memory method, the division is not limited to this example. As shown in FIG. 9A, general grouping may be made. This is such re-division that the boundary between the two illumination light selection areas MR2a and MR2b becomes a straight line or the like. In this case, if such a configuration is adopted that 75% or more of each of the newly divided illumination light selection areas MR2a and MR2b is connected to the desired exit end OEa, OEb of the light guide 232, the advantageous effect of the present invention can fully be received. By doing so, the control of the mirror elements 354 by the DMD control circuit 344 can be simplified, and the information to be stored in the memory 462 can be decreased.

Note that in the advance memory method, there is no need to exactly group all mirror elements 354 in association with the first exit end OEa and second exit end OEb. For example, when only the first mirror element group 354Ga and the memorized mirror elements 354 are changed to the first state, if the light quantity of illumination light radiated from the first exit end OEa to the illumination target is ten times or more greater than the light quantity of illumination light radiated from the second exit end OEb to the illumination target, advantageous effects can fully be exhibited. In addition, if the light quantity is two times or more, the advantageous effects can be received. Specifically, even if the positional relationship between the entrance end IE of the light guide 232 and the digital mirror device 350 is slightly displaced due to attachment/detachment of the scope 200, or the like, the advantageous effects of the present invention can be obtained.

Thus, in the (A) advance memory method, when a mirror element 354 is set in the first state, if illumination light is emitted from both the first illumination lens 212 and the second illumination lens 212, this mirror element 354 can be memorized in the memory 462 as a mirror element belonging to both the group corresponding to the first illumination lens 212 and the group corresponding to the second illumination lens 212. By doing so, illumination light can efficiently be utilized.

On the other hand, such a mirror element 354 can be memorized in the memory 462 as a mirror element belonging to neither group. By doing so, for example, the ratio of light quantities can be set so that the light quantity emitted from the first illumination lens 212 becomes greater than the light quantity emitted from the second illumination lens 212.

In addition, when a mirror element 354 is set in the first state, if illumination light is emitted from neither the first exit end OEa nor the second exit end OEb, this mirror element 354 is normally memorized as a mirror element belonging to neither group. However, when all mirror elements 354 around this mirror element 354 belong to one of the groups, this mirror element 354 can be memorized as belonging to this group. Specifically, at the entrance end IE of the light guide 232, although the entrance apertures of optical fibers are located, there are predetermined gaps (FIG. 2). Thus, when illumination light reflected by a mirror element 354 is not emitted from any of the illumination lenses 212, it is possible that this is due to radiation on such gaps. This being the case, when peripheral mirror elements 354 belong to either of the groups, this mirror element 354 is also memorized as belonging to this group, and thereby illumination light can efficiently be utilized.

By the above (A) advance memory method, it is possible to acquire state information of the mirror elements 354 of the digital mirror device 350, the state information being necessary for the switching control of illumination light that is emitted from the two illumination light emission units 210 provided in the distal section 202a of the scope 200. The state information, described here, of the mirror elements 354 of the digital mirror device 350 refers to arrangement information of the first illumination light selection area MR2a that is the area of the mirror elements 354 that cause illumination light to be emitted from the first illumination light emission unit 210, and the second illumination light selection area MR2b that is the area of the mirror elements 354 that cause illumination light to be emitted from the second illumination light emission unit 210.

Accordingly, when a luminance distribution of an image, for instance, is to be adjusted, for example, when the side of the first illumination lens 212 is excessively bright, part of the mirror elements 354 belonging to the group corresponding to the first illumination lens 212 are changed to the second state, and thereby the light distribution can be optimized and blown-out highlights or the like of an image can be suppressed. Specifically, among the mirror elements 354 belonging to the first mirror element group 354Ga, by changing the ratio of mirror elements 354 that are in the first state, the brightness of the image on the first illumination lens 212 side can be adjusted. Similarly, among the mirror elements 354 belonging to the second mirror element group 354Gb, by changing the ratio of mirror elements 354 that are in the first state, the brightness of the image on the second illumination lens 212 side can be adjusted.

The method described here is merely an example of the (A) advance memory method. For example, classification may be made while directly observing the illumination light emission unit 210 of the distal section 202a of the insertion section 202. According to this method, simply by changing one mirror element 354 in the first state only once, the mirror element 354 can be classified into either the first mirror element group 354Ga or the second mirror element group 354Gb.

In addition, without using a shielding cover, grouping may be made while imaging a scattering plate or a fluorescent plate. In this case, the mirror elements 354 are not grouped based on the illumination light emitted from the first and second exit ends OEa and OEb, but are grouped based on a region of an image IMG.

FIG. 10 shows an example of an image that is captured by the endoscope system 100 and is displayed on the monitor 390. For example, in FIG. 10, the mirror elements 354 may be grouped into mirror elements 354 that contribute to illuminating a right region IRR of the image IMG, mirror elements 354 that contribute to illuminating a central region ICR, and mirror elements 354 that contribute to illuminating a left region ILR. For example, the left region ILR is a first illumination region in which first illumination light emitted from the first illumination light emission unit 210 is dominant. The right region IRR is a second illumination region in which second illumination light emitted from the second illumination light emission unit 210 is dominant. The central region ICR is a common illumination region in which first illumination light and second illumination light are in substantially equal degrees.

Further, the light distribution correction information deriving circuit 378 may derive control information of the digital mirror device 350, based on the relationship among luminance values of the right region IRR, central region ICR, and left region ILR. Alternatively, the light distribution correction information deriving circuit 378 may derive control information of the digital mirror device 350, based on a luminance value of a shadow appearing in a projection portion or a recess portion of an observation target existing in the central region ICR.

Thereby, when the brightness/darkness of the endoscopic image is adjusted, the light quantity of the radiation region can directly be changed. For example, when the right side of the image is too bright, the brightness of the image can be adjusted by setting part of the group of the mirror elements 354 that contribute to illuminating the right region in the second state.

In FIG. 10, the image IMG is divided into three regions. Alternatively, it may be configured that the image IMG are divided into a first region in which the first illumination light is dominant, and a second region in which the second illumination light is dominant, and the mirror elements 354 are grouped into mirror elements 354 contributing to illuminating the first region and mirror elements 354 contributing to illuminating the second region.

Moreover, in the above-described example, each of the mirror elements 354 is classified into the first mirror element group 354Ga or the second mirror element group 354Gb, and memorized, but the embodiment is not limited to this example. 2×2 or 10×10 mirror elements 354 may be gathered and classified, and memorized. In this case, as regards the classification into the first mirror element group 354Ga or the second mirror element group 354Gb, it is also preferable to compare the light quantity emitted from the first illumination lens 212 and the light quantity emitted from the second illumination lens 212, and to classify the mirror elements into the mirror element group corresponding to the greater light quantity. Further, it is preferable to use the light quantity ratio itself as an index of classification, and to perform such classification that when the light quantity ratio is 3:1, the ratio of the first mirror element group 354Ga is 75%, and the ratio of the second mirror element group 354Gb is 25%.

By the above configuration, the light quantity ratio of illumination light emitted from the illumination lenses 212 included in the insertion section 202 can be adjusted, and the brightness of the image displayed on the monitor 390 can properly be adjusted.

It is preferable that the work by the advance memory method is performed before shipment or at a time of delivery of the endoscope system 100. In addition, it is preferable to automatically perform the work, each time the scope 200 is replaced.

If the work is performed before shipment or at a time of delivery, a user work is made unnecessary, and a setup time at a time of replacing the scope 200 can be reduced. On the other hand, if the work is performed each time the scope 200 is replaced, the influence of a positional displacement or the like at the time of attachment/detachment of the scope 200 can be canceled, and more precise light distribution control can be executed.

Second Embodiment

Hereinafter, a second embodiment of the present invention will be described. A description of the configuration common to the first embodiment is omitted.

[Configuration]

The configuration of the endoscope system of the present embodiment is basically common to the configuration of the endoscope system 100 of the first embodiment. Accordingly, in the description of the present embodiment, too, the endoscope system is expressed as the endoscope system 100. Further, the constituent components are also denoted by the same reference signs as in the first embodiment.

The present embodiment differs from the first embodiment with respect to the procedure of light distribution control. The first embodiment illustrates the method in which the mirror elements 354 of the digital mirror device 350 are grouped into the first mirror element group 354Ga, which is the group that brings illumination light to the first illumination lens 212, and the second mirror element group 354Gb, which is the group that brings illumination light to the second illumination lens 212, and the light distribution of illumination light emitted from the distal end of the scope 200 is controlled by controlling the ratio of light quantities emitted from the respective illumination lenses 212. By contrast, the present embodiment illustrates an example of using a (B) feedback method in which, during the observation of the endoscopic image, adjustment to a proper light distribution is executed in real time, while confirming the variation of the luminance distribution of the image at a time when the state of each mirror element 354 is switched.

The feedback method is a method of controlling the mirror elements 354 included in the mirror array 352 of the digital mirror device 350, based on the brightness/darkness or the like of the image acquired by using the endoscope system 100.

In the endoscope system 100 for medical use, mainly, the insertion section 202 of the scope 200 is inserted into a body cavity, and an image of the space in the body or the inner surface of a tubular organ is acquired. For example, in a gastroscopy examination, the insertion section 202 of the scope 200 is inserted from the mouth or nose. A distal end of the insertion section 202 of the scope 200 comes in contact with a wall of the mouth or nose, and advances to the pharynx and to the gullet while being in close proximity. In a central part of an image at this time, since a forward part of the lumen such as the gullet existing in a direction of advancement appears, the luminance of the central part of the image lowers, and the image becomes a dark image. On the other hand, a side wall of the gullet is located in a peripheral part of the image. In general, the gullet has a thickness of approximately 2 to 3 cm. Thus, the side wall of the gullet located in the peripheral part of the image is very near, compared to the opening of the gullet located at the center.

As a result, in the conventional endoscope system, for example, if the light quantity is set for the opening of the gullet at the center of the image, the gullet side wall located at the periphery becomes too bright, and, in some cases, blown-out highlights (a state in which a tolerable light reception amount of the imaging element 224 is exceeded) occur in the image. Conversely, if the light quantity is set for the gullet side wall, a forward part of the gullet becomes dark, and the image becomes difficult to observe.

In this case, with the use of the endoscope 100 according to the present invention, the brightness of the entire screen can be optimized by increasing the brightness of the forward part of the gullet and decreasing the light quantity of the side part.

In order to execute this light distribution control, the feedback method to be described below is excellent. In the feedback method, partial dimming can be performed such that an excessively bright area on the screen becomes dark.

(B) "Feedback Method"

Figure 11A:
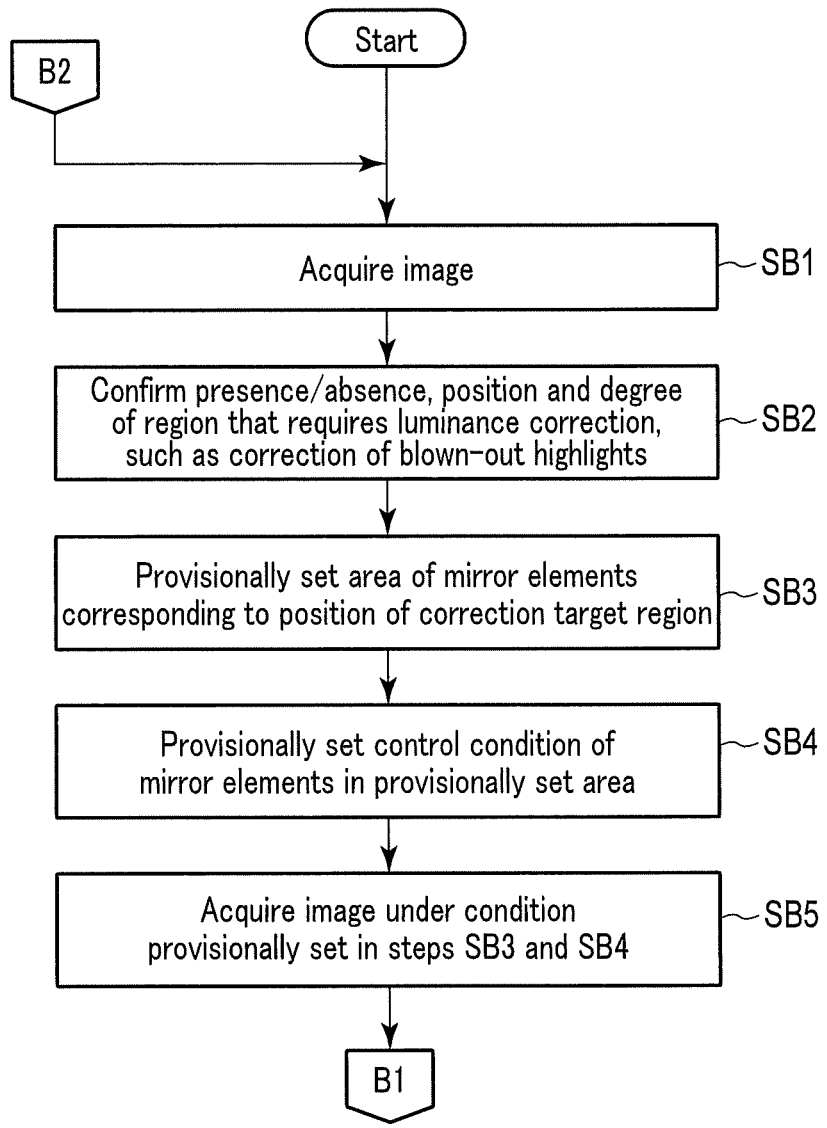
FIG. 11A shows a first half of a flowchart illustrating a procedure of light distribution control by a feedback method.
Figure 11B:
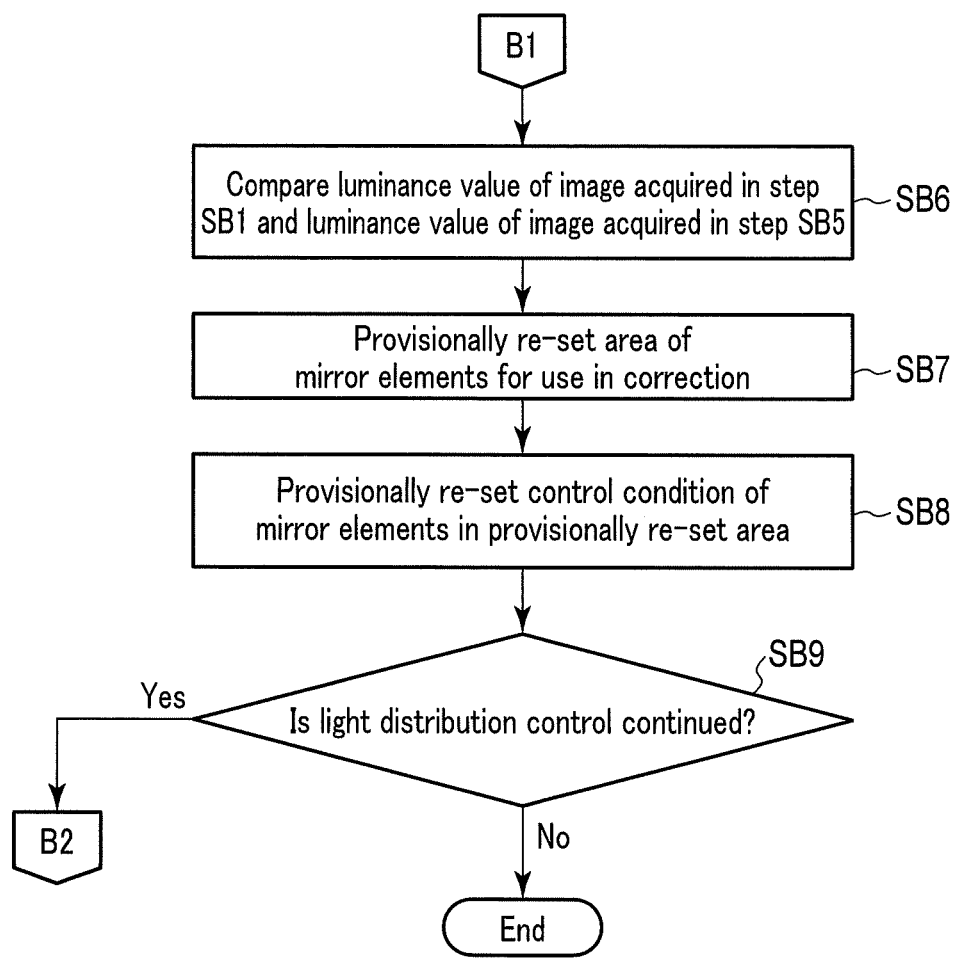
FIG. 11B shows a second half of the flowchart illustrating the procedure of the light distribution control by the feedback method.
Figure 12:
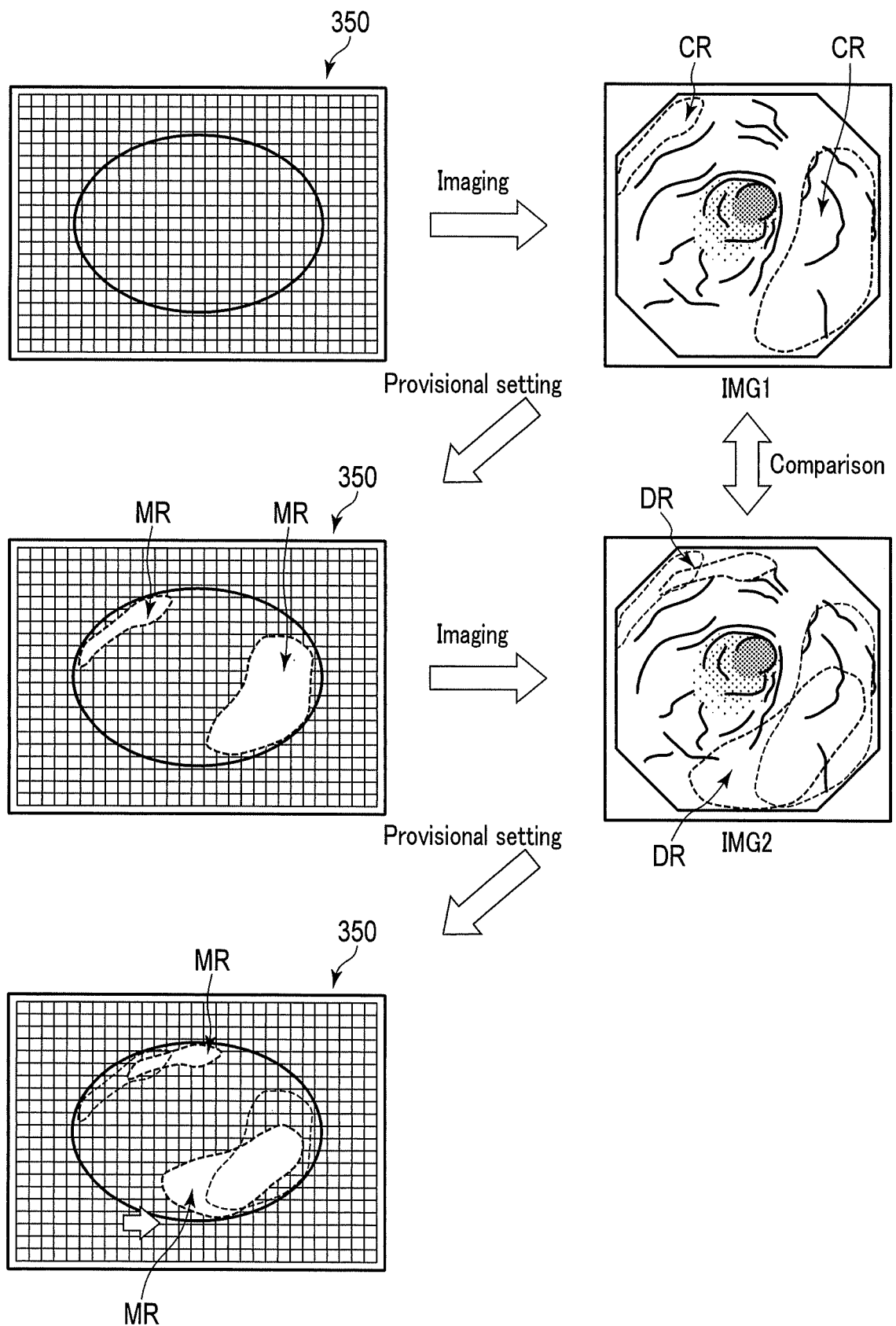
FIG. 12 schematically shows states of mirror elements in initial steps of the light distribution control by the feedback method, and images that are acquired.

Next, the (B) feedback method will be described with reference to FIG. 11A, FIG. 11B, and FIG. 12, by describing the steps one by one. FIG. 11A and FIG. 11B respectively show a first half and a second half of a flowchart illustrating the procedure of light distribution control by the feedback method. FIG. 12 schematically shows states of mirror elements in initial steps of the light distribution control by the feedback method, and images that are acquired.

(Step SB1: Acquisition of image)

In step SB1, an image is acquired based on a normal image acquisition process. This image is provisionally referred to as "first image IMG1". At this time, the state of the mirror elements 354 of the digital mirror device 350 is also stored in the memory 462.

Figure 13A:
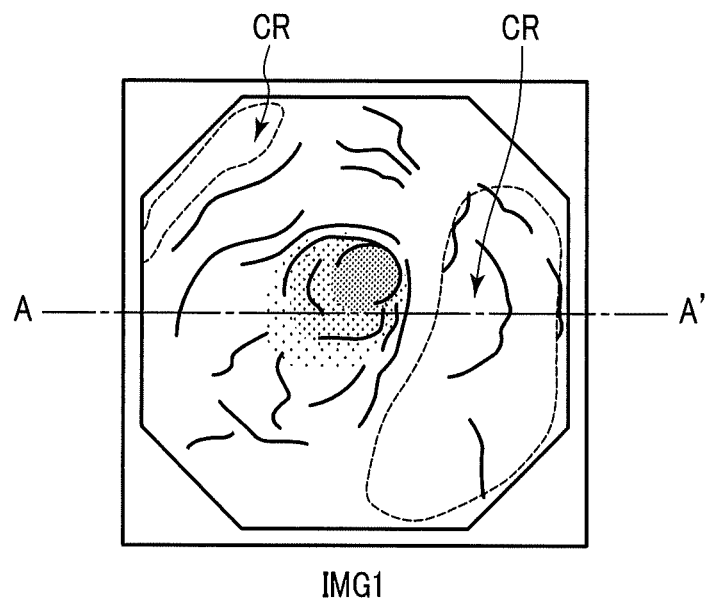
FIG. 13A shows an image that is first acquired in the light distribution control by the feedback method.
Figure 13B:
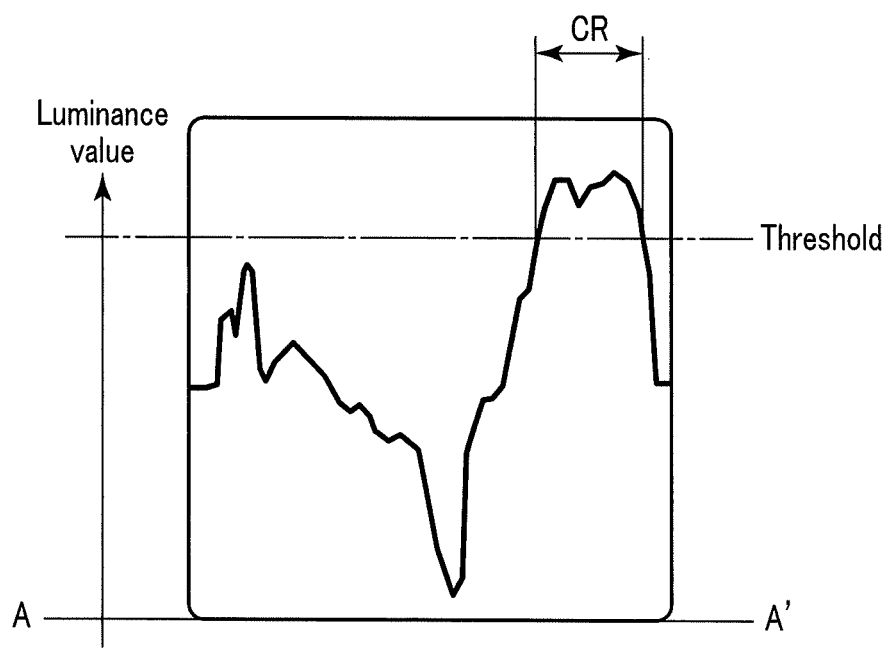
FIG. 13B shows a luminance value in pixels on a line A-A' of the image shown in FIG. 13A.

(Step SB2: Confirmation of presence/absence, position and degree of region that requires luminance correction, such as correction of blown-out highlights) In step SB2, based on luminance information of the acquired first image, a region having a luminance exceeding a predetermined threshold is extracted as a correction target region. FIG. 13A and FIG. 13B show image views of the extraction of the correction target region. FIG. 13A shows the first image IMG1, and FIG. 13B shows a luminance value in pixels on a line A-A' of the first image IMG1 shown in FIG. 13A. In the graph of the luminance value shown in FIG. 13B, a region of a predetermined threshold or more is extracted as a correction target region CR. Although FIG. 13A and FIG. 13B show an example of one cross section for the purpose of simplicity, a similar process is executed over the entire image in the extraction of the correction target region CR.

The predetermined threshold can be set as appropriate, based on the dynamic range of the imaging element 224, the favor of the worker, etc. Here, in some cases, the endoscope system 100 is used for observation of a mucous membrane that a living body has, or a treatment instrument such as a forceps. Thus, blown-out highlights may occur due to regular reflection of illumination light by the surface of the mucous membrane, or regular reflection of illumination light by a metallic surface of the treatment instrument. In general, since the size of a luminescence spot on the image is small and the influence on observation is small, the blown-out highlights can be excluded from the correction target. Whether blown-out highlights are excluded from correction targets or treated as a correction target can be determined as needed, based on the favor of the worker or in the system setup.

The light distribution correction information deriving circuit 378 extracts the correction target region CR whose light quantity is to be corrected, from among regions having luminances exceeding the predetermined threshold. Then, with respect to the extracted correction target region CR, the degree of blown-out highlights (luminance value of the image) and the position on the image (address of pixels) are stored in the memory 462.

In the present embodiment, the upper limit of the luminance value is set, and the region of the upper limit or more is extracted as the correction target region CR, but the embodiment is not limited to this. It is also preferable that the lower limit of the luminance value is set, and a region lower than the lower limit is extracted as the correction target region CR.

(Step SB3: Provisional Setting of Area MR of Mirror Elements Corresponding to the Position of Correction Target Region CR)

In the distal section 202a of a general scope 200, the imaging element 224 and light guide 232 are directly or indirectly fixed to a common member. In addition, in the LG connector 410, an end of the light guide 232 is fixed to the optical system in the light source box 310 so that the center axis of the light guide 232 substantially coincides with the optical axis of illumination light. In this case, the light guide 232 is attached rotatably around the optical axis, or attached unrotatably by a rotation-preventing mechanism such as a stopper. In the present embodiment, the description is given by taking the latter as an example. In the case of the former, it should suffice if, in this description, the mirror array 352 of the digital mirror device 350 and the image are correlated by taking into account the rotation of the light guide 232 around the center axis, each time the LG connector 410 is attached/detached.

In step SB3, the correspondence relation between the position on the first image IMG1 and the radiation position of illumination light through the mirror elements 354 of the digital mirror device 350 is provisionally set. Thereby, an area MR of the mirror elements 354 used for correction, which is estimated to correspond to the position of the correction target region CR on the first image IMG1, is provisionally set. In other words, the mirror elements 354 used for correction are provisionally selected.

For example, it may be configured that the information at a time when the scope 200 has been previously used and that is stored in the memory 462 is called, and a generally corresponding position is provisionally set. In addition, provisional setting may be made based on the grouping information of the mirror elements 354 contributing to emission of illumination light from the first illumination lens 212 and the mirror elements 354 contributing to emission of illumination light from the second illumination lens 212, the grouping information being set based on the (A) advance memory method described in the first embodiment. Furthermore, mirror elements 354 at a freely chosen position among the mirror elements 354 on the mirror array 352 of the digital mirror device 350 can be selected. In this case, the size of the area MR of the selected mirror elements 354 can be set based on the shape and size of the correction target region CR on the image.

(Step SB4: Provisional Setting of Control Condition of Mirror Elements 354)

In step SB4, a control condition of the mirror elements 354 in the provisionally set area is provisionally set. With respect to the region on the image with the luminance value exceeding the predetermined threshold, the light distribution correction information deriving circuit 378 adjusts, based on the degree of exceeding of the threshold (e.g. slightly exceeding, greatly exceeding), the ratio between the first state and second state of the mirror elements 354 existing in the region, the ratio being included in the light distribution correction information. As shown in FIG. 14A, for example, as regards a region in which the degree of blown-out highlights slightly exceeds a predetermined threshold Th1, a ratio ε of the first state/second state of the mirror elements 354 (the ratio of mirror elements 354 in the first state, among all mirror elements 354 existing in the correction target area CR) is set at, for example, 75%. As regards a region in which the degree of blown-out highlights is considerably high and blown-out highlights occur in almost all pixels, the ratio ε of the first state/second state is set at 50%. In this manner, the ratio of mirror elements 354 that are set in the first state is set in accordance with the degree of the blown-out highlights. Here, a ratio change threshold Th2 that is a criterion for changing the ratio ε of the first state/second state may be set at, for example, a midpoint between the threshold Th1 and a light reception upper limit value Th1 of the imaging element 224. Note that it is preferable to set mirror elements 354 that are to be set in the second state, such that these mirror elements 354 are dispersed in the entire correction target region CR. Further, when the region includes regions with different degrees of blown-out highlights, the regions may be further divided based on the degrees of blown-out highlights, and mirror elements 354 that are to be set in the second state can be selected with respect to each region after the further division.

(Step SB5: Control of Digital Mirror Device 350 by Provisional Setting, and Acquisition of Image)

In step SB5, based on the DMD control information that is the light distribution correction information that is provisionally set in steps SB3 and SB4, the digital mirror 350 is controlled and an image is acquired. Like step SB1, the process of image acquisition is performed like normal image acquisition. The acquired image is provisionally referred to as "second image IMG2". Needless to say, the light distribution of the second image IMG2 is different from that of the first image IMG1.

(Step SB6: Confirmation of Change of Luminance Value)

In step SB6, the luminance value of the first image IMG1 acquired in step SB1 is compared with the luminance value of the second image IMG2 acquired in step SB5. The result of the change of the state of the mirror elements 354 provisionally set in steps SB3 and SB4 appears as the change of the luminance values of the two images. The region with the changed luminance value corresponds to the DMD control information (the region in which the state of mirror elements 354 is changed, and the ratio of the first state/ second state) on the surface of the mirror array 352 of the digital mirror device 350, which is provisionally set in steps SB3 and SB4. The light distribution correction information deriving circuit 378 compares the luminance value of the first image IMG1 and the luminance value of the second image IMG2, correlates a region DR on the image having the changed luminance value with the DMD control information provisionally set in steps SB3 and SB4, and extracts the region DR as a luminance distribution change region. Specifically, distribution information of luminance values of the first image IMG1 and second image IMG2 is created, and a difference is calculated. Thereby, a region with a changed luminance value can be extracted. For example, in FIG. 12, the region DR is a region where the luminance distribution is different between the first image IMG1 and second image IMG2, and corresponds to a region in which the correction target region CR of the first image IMG1 is rotated by approximately 20° clockwise. This result is stored in the memory 380 in the camera control unit 370.

(Step SB7: Provisional Re-Setting of Area MR of Mirror Elements 354 for Use in Correction)

In step SB7, the positional relationship between the correction target region CR extracted in step SB2, the area MR of the mirror elements 354 provisionally set in step SB3, and the region with the actually changed luminance value, which is confirmed in step SB5, is confirmed, and the area MR of mirror elements 354 for use in correction is provisionally set once again. Specifically, the light distribution correction information deriving circuit 378 derives the light distribution correction information that is the arrangement information of the mirror elements 354 whose states are to be switched for luminance value correction, by comparing the first image IMG1 and second image IMG2. For example, in FIG. 12, the area MR of mirror elements 354 that is provisionally re-set and used for correction corresponds to an area in which the area MR of mirror elements 354 that is first provisionally set and used for correction is rotated by approximately 20° clockwise.

(Step SB8: Provisional Re-Setting of Control Condition of Mirror Elements 354)

In step SB8, the control condition of the mirror elements 354 that are located in the provisionally re-set area and used for correction is provisionally set once again.

(Step SB9: Judgment of Continuation of Light Distribution Control)

In step SB9, it is judged whether or not to continue the light distribution control. When the light distribution control is not continued, the process is finished. When the light distribution control is continued, the process returns to step SB1, and an image is acquired in steps SB6 and SB7, based on the provisionally re-set DMD control information.

Thereafter, in step SB2, if there is a need to change the light distribution due to blown-out highlights or the like, the flow from step SB2 is continued.

In addition, as a result of the provisional re-setting in steps SB6 and SB7, if there are no blown-out highlights or the like in the image acquired after returning to step SB1, or if the area MR of the mirror elements 354 provisionally set in step SB3 is substantially equal to the area MR of the mirror elements 354 provisionally re-set in step SB6 and the correction target region CR disappears, the process returns to step SB1 and an image is acquired. Then, assuming that the correction is completed, the flow is suspended, and step SB2 is continued until there occur blown-out highlights or the like of a level that requires the next correction. (See FIG. 14B.)

FIG. 14B schematically shows a state in which the correction target region CR, which exists in a pre-correction luminance distribution Ds1, disappears in a post-correction luminance distribution Ds2.

By the above configuration, in addition to the advantageous effects of the first embodiment, it becomes possible to adjust the light quantity in accordance with the correction target region CR of the luminance value, including a region of blown-out highlights on the image. In addition, during the observation, the feedback to the image can be performed in real time.

In FIG. 12, for the purpose of simplicity, the correction target region CR on the image and the mirror element area to be corrected on the mirror array surface of the digital mirror device 350 are depicted as having similar shapes, but the embodiment is not limited to this. Various positional relationships are conceivable, based on the relationship or the like of dispositions of the entrance end OE and the exit end OEa, OEb of the light guide 232. However, in such cases, too, the (B) feedback method described here can be used.

Third Embodiment

Figure 15:
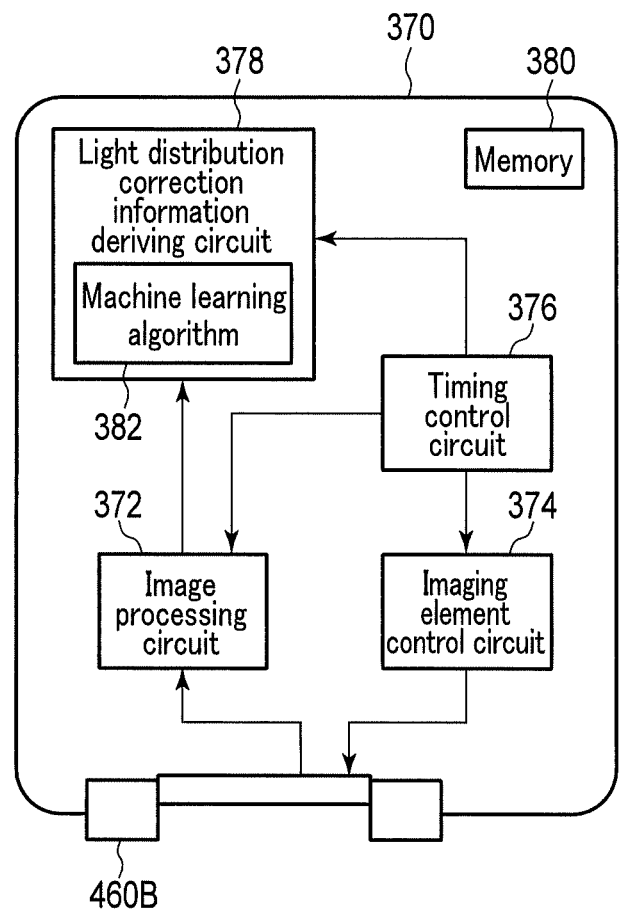
FIG. 15 schematically shows a configuration of a camera control unit including a light distribution correction information deriving circuit including a machine learning algorithm.

The second embodiment illustrates the example in which the light distribution correction information deriving circuit 378 derives, by the (B) feedback method, the light distribution correction information for controlling the state of the digital mirror device 350, which is used for correction. As shown in FIG. 15, the present embodiment differs from the second embodiment in that the light distribution correction information deriving circuit 378 included in the camera control unit 370 includes a machine learning algorithm 382.

The machine learning refers to a technology/method that aims at realizing the same function as the learning ability of a human by a computer. Specifically, in the present embodiment, machine learning algorithms are used for the following two:

(1) A machine learning algorithm configured to extract a region with an excessively high luminance and a region with an excessively low luminance with respect to an endoscopic image; and (2) A machine learning algorithm configured to update the state of mirror elements 354 of the digital mirror device 350, and to correct a region with an excessively high luminance and a region with an excessively low luminance with respect to an endoscopic image.

The feature of the machine algorithm resides in that programming is not explicitly performed, but the ability to learn is given to a computer or the like. In the present embodiment, the light distribution correction information deriving circuit 378 has the ability to learn.

As regards the machine learning algorithm of (1), an endoscopic image is given as an input, and information is provided so as to perform judgment by the luminance value of an image as a feature.

As regards the machine learning algorithm of (2), information of the positions and degrees of a region with an excessively high luminance and a region with an excessively low luminance on an endoscopic image is given as an input, and information of the state of mirror elements 354 of the digital mirror device 350 (the distribution information of the mirrors in the first state and second state of the mirror elements 354 in the mirror element existence area MR2, which corresponds to the connected scope, on the digital mirror device 350) is provided as a feature.

In the present embodiment, various algorithms of machine learning/deep learning can be utilized. For example, as regards the above (1) and (2), it is preferable to perform unsupervised learning. When supervised learning is performed, it is preferable to perform learning by adding information as follows.

When the supervised learning is performed as regards (1), information is provided to the machine learning algorithm by setting, in advance, with respect to some images, "OK" for a case in which the luminance value of an image is within a proper range, and setting "NG" for a case in which the luminance value of an image is outside the proper range.

When the supervised learning is performed as regards (2), there are provided, in advance, a plurality of sets of state information of the mirror elements 354 of the digital mirror device 350 and luminance information on the image at that time.

Further, various machine learning algorithms, such as reinforcement learning (Q learning), can be used.

According the present embodiment, light distribution control corresponding to various situations can be performed without creating an algorithm configured to derive light distribution correction information for light distribution control.

[Supplement]

The functions of the digital mirror device 350 in the present invention are basically the following three:

(1) ON/OFF of illumination light, (2) Reduction of peripheral light that does not enter an entrance aperture of the light guide 232, and (3) Light distribution control.

Among these, the (3) light distribution control has been already described. The other two will be described below.

(1) "ON/OFF of Illumination Light" When all mirror elements 354 in the mirror element existence area MR2 that can bring light into the light guide 232 are in the first state, a greatest quantity of laser light emitted from the laser light sources LD1 to LD4 is reflected toward the entrance end IE of the light guide 232, and exits the exit ends OEa and OEb of the light guide 232. Specifically, when the laser light quantities emitted from the laser light sources LD1 to LD4 are equal, brightest illumination light exits the exit ends OEa and OEb of the light guide 232.

In addition, all mirror elements 354 in the mirror element existence area MR2 are in the second state, all laser light emitted from the laser light sources LD1 to LD4 reaches the light stopper 324, and is absorbed by the light stopper 324 and converted to heat. Specifically, even if the laser light sources LD1 to LD4 are turned on, no illumination light exits the exit ends OEa and OEb of the light guide 232, like a state similar to the OFF state. At this time, all laser light is absorbed by the light stopper 324. In this manner, by the state control of the digital mirror device 350, the laser light can be turned on/off. In this case, the switching speed of the digital mirror device 350 is about microseconds and is very high, and thus the ON/OFF control of illumination light can be executed at high speed.

(2) "Reduction of Peripheral Light that does not Enter the Entrance Aperture of the Light Guide 232"

Figure 16A:
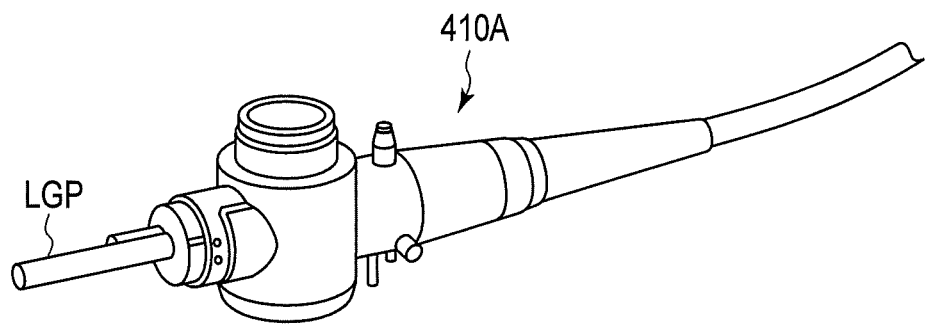
FIG. 16A shows a vicinity of an entrance aperture of a light guide of an LG connector portion of a scope of a general endoscope system.
Figure 16B:
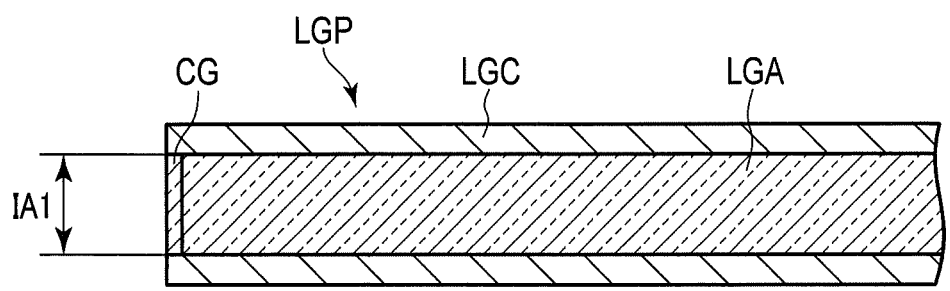
FIG. 16B shows a cross-sectional configuration of an LG post in which a large-diameter light guide is mounted.
Figure 16C:
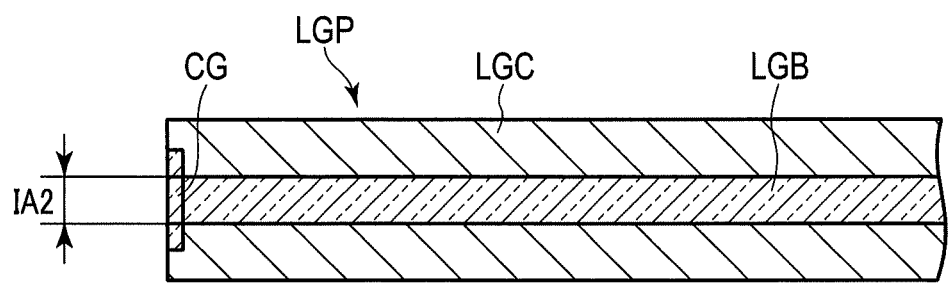
FIG. 16C shows a cross-sectional configuration of an LG post in which a small-diameter light guide is mounted.

FIG. 16A shows a vicinity of an entrance aperture of a light guide of an LG connector portion 410A of a scope of a general endoscope system. FIG. 16B and FIG. 16C show cross-sectional configurations of an LG post LGP shown in FIG. 16A. FIG. 16B shows an LG post LGP in which a large-diameter light guide LGA is mounted. FIG. 16C shows an LG post LGP in which in which a small-diameter light guide LGB is mounted.

The entrance end of the light guide LGA, LGB is the LG post LGP projecting from the LG connector portion 410A. The light guide LGA, LGB is disposed in the LG post LGP, and the outer surface of the light guide LGA, LGB is protected by an LG outer sheath LGC such as a stainless pipe. In addition, a cover glass CG is provided on the entrance end of the light guide LGA, LGB, and protects the entrance apertures of optical fibers that constitute the light guide LGA, LGB.

In the scope of the endoscope system, the thickness of the light guide LGA, LGB varies depending on the purpose of use and kinds. In general, in a large-diameter scope such as a peroral endoscope system or a colonoscope system, the large-diameter light guide LGA is mounted as shown in FIG. 16B. On the other hand, in a small-diameter scope such as a transnasal endoscope system, the small-diameter light guide LGB is mounted as shown in FIG. 16C. Note that in the large-diameter light guide LGA and the small-diameter light guide LGB, the numbers of bundled optical fibers are different, and, in general, optical fiber elements of the same thickness are used.

On the other hand, the light source box of a general endoscope is configured to emit illumination light in accordance with an entrance aperture IA1 of the large-diameter light guide LGA of the large-diameter scope. Accordingly, when the small-diameter scope is connected, illumination light is radiated also on the periphery of the entrance aperture IA2 of the small-diameter light guide LGB. In some cases, such problems arise that the illumination light radiated on the periphery of the entrance aperture IA2 is absorbed by a member such as the LG outer sheath LGC and converted to heat, thus raising the temperature of the LG post LGP rises, or illumination light is scattered and travels into the light source box, thus raising the temperature of a member that is not expected, or light leaks to the outside.

In the present embodiment, when the scope 200 and main body 300 are connected, the main body 300 reads out identification (ID) information of the scope 200 stored in the memory 462 included in the CCU connector 460, and recognizes the size of the entrance aperture of the light guide 232 of the connected scope 200. In accordance with the entrance aperture, among the mirror elements 354 of the digital mirror device 350, mirror elements 354 corresponding to the entrance end IE of the light guide 232 of the connected scope 200 are set in the first state, and mirror elements 354 located therearound are set in the second state. Thereby, as shown in FIG. 7, even in the case of the small-diameter scope, such a configuration is achieved that the laser light is radiated on only the entrance aperture of the light guide 232.

Thereby, the temperature of the LG post LGP is not raised more than necessary, and unnecessary scattered light or the like into the light source box 310 can be reduced.

[Supplement 2]

(Light Source is not Limited to Laser Light Sources LD1 to LD4)

In all of the above-described embodiments, the laser light sources LD1 to LD4 are used as the light source in the light source unit 320, but the embodiments are not limited to this. For example, also when a Xe lamp, a halogen lamp, a white LED, LEDS of different colors such as RGB, or a super-luminescent diode is used, the advantageous effects can be obtained. Besides, only one kind of light source may be used, or a plurality of kinds of light sources may be used in combination.

Using the laser light sources LD1 to LD4 allows a substantially parallel beam of illumination light to enter the digital mirror device 350, and so as to efficiently bring the light into the light guide 232. As a result, the endoscope system 100 with very high efficiency can be provided.

In addition, by using the white LED or super-luminescent diode, the endoscope system 100 having a lower power consumption than the lamp and compatibly having both efficiency and color rendering properties can be fabricated.

Figure 17:
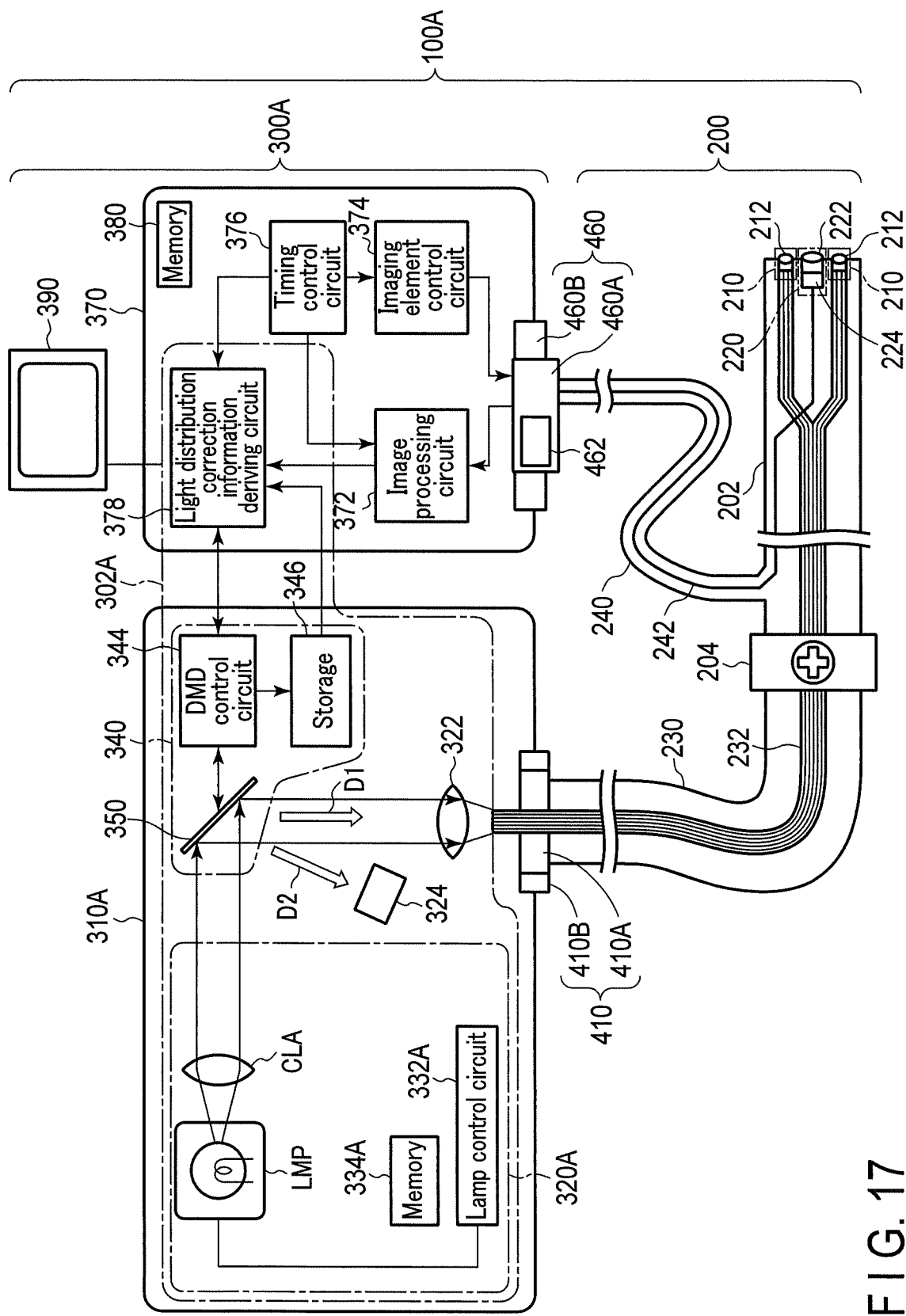
FIG. 17 shows an example of an endoscope system in which a Xe lamp is used as a light source.

FIG. 17 shows an example of an endoscope system 100A in which a Xe lamp is used as a light source. In FIG. 17, members denoted by the same reference signs as those shown in FIG. 1 are similar members, and a detailed description thereof is omitted. Hereinafter, different parts will mainly be described.

As illustrated in FIG. 17, the endoscope system 100A includes a scope 200, and a main body 300A including an illumination light supply device 302A. The main body 300A includes a light source box 310A, a camera control unit 370, and a monitor 390.

Even when a Xe lamp LMP is used as the light source, the configurations of the camera control unit 370, scope 200, monitor 390, and the like are basically unchanged. The image processing circuit 372, etc. are adjusted for the Xe lamp LMP, when necessary.

In addition, the light source box 310A includes a light source unit 320A. The light source unit 320A includes the Xe lamp LMP configured to emit illumination light; a collimate lens CLA configured to collimate the illumination light emitted from the Xe lamp LMP; a lamp control circuit 332A configured to control the operation of the Xe lamp LMP; and a memory 334A configured to store necessary information for control. The other configuration is basically the same as the light source box 310 shown in FIG. 1.

A filter for eliminating infrared or ultraviolet emitted from the Xe lamp LMP, a cooling mechanism for the Xe lamp LMP, and a member or the like mounted in the Xe light source for an ordinary endoscope may be properly assembled as needed. In addition, although FIG. 17 shows the example in which the light stopper 324 is provided, the light stopper 324 may be removed. Thereby, the size of the light source box 310 can be reduced.

By using the Xe lamp LMP or a halogen lamp as the light source, illumination light having a very broad spectrum can be obtained. Thereby, the endoscope system 100A with excellent color reproducibility can be provided.

(Light Quantity Distribution Changing Device is not Limited to Digital Mirror Device 350)

Although the example in which the digital mirror device 350 is used as the light quantity distribution changing device has been illustrated, the light quantity distribution changing device is not limited to this. For example, a reflective or transmissive liquid crystal device (LCD) may be used as the light quantity distribution changing device.

Figure 18:
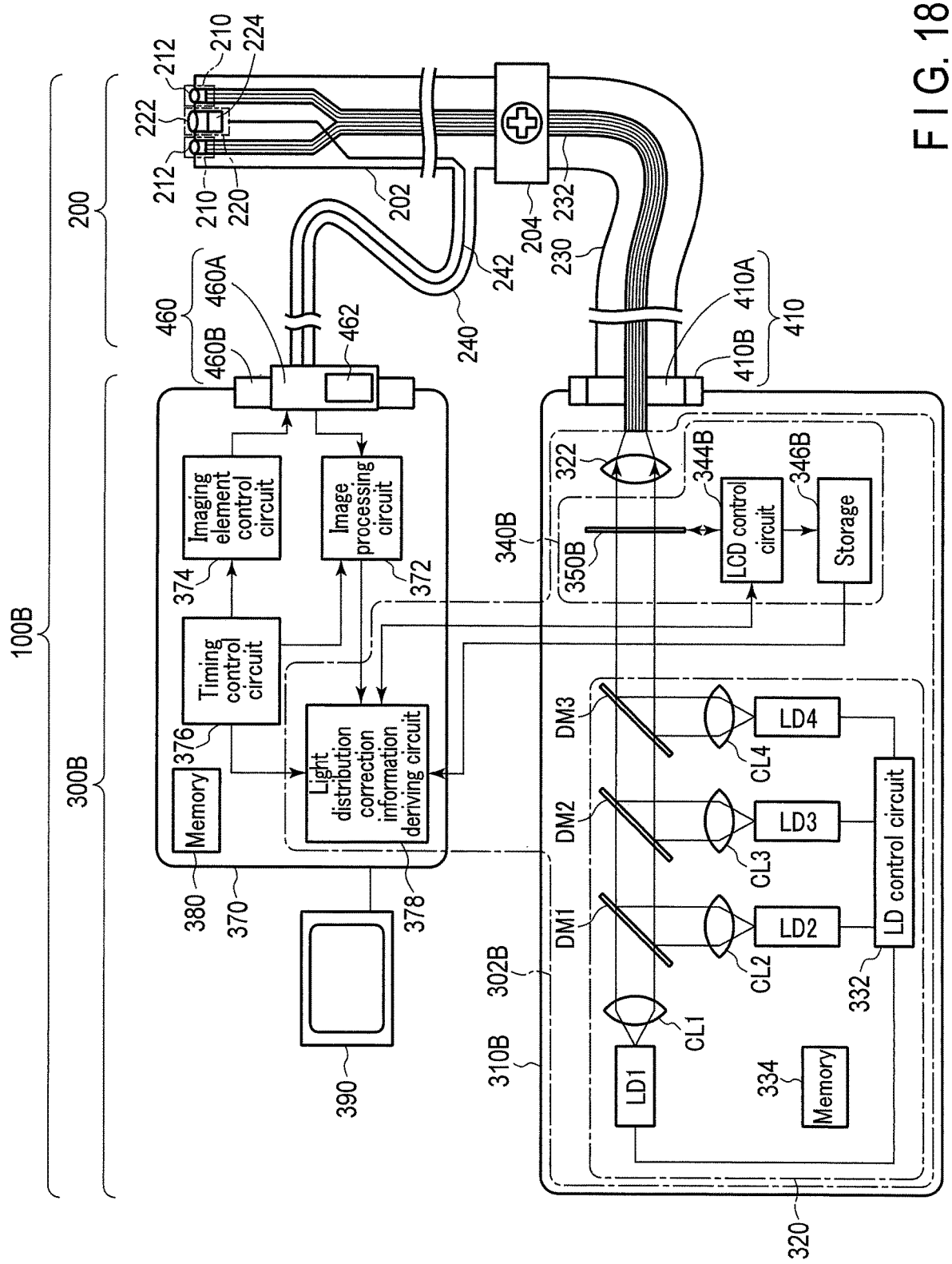
FIG. 18 shows an example of an endoscope system in which a transmissive liquid crystal device is used as a light quantity distribution changing device.

FIG. 18 shows an example of an endoscope system 100B in which a transmissive liquid crystal device is used as the light quantity distribution changing device. In FIG. 18, members denoted by the same reference signs as those shown in FIG. 1 are similar members, and a detailed description thereof is omitted.

The basic configuration of the endoscope system 100B is similar to that of the endoscope system 100 using the digital mirror device 350 shown in FIG. 1. Basically, the endoscope system 100B has a configuration in which the DMD unit 340 shown in FIG. 1 is replaced with a liquid crystal device unit 340B.

Specifically, as shown in FIG. 18, the endoscope system 100B comprises a scope 200, and a main body 300B including an illumination light supply device 302B. The main body 300B includes a light source box 310B, a camera control unit 370, and a monitor 390.

The light source box 310B includes a light source unit 320 configured to emit illumination light, and the liquid crystal device unit 340B configured to adjust a light quantity distribution of the illumination light emitted from the light source unit 320. The liquid crystal device unit 340B includes a transmissive liquid crystal device 350B that is a light quantity distribution changing device disposed on an optical path of the illumination light emitted from the light source unit 320; a liquid crystal device (LCD) control circuit 344B configured to control the transmissive liquid crystal device 350B; and a liquid crystal device control information storage 346B configured to store control information of the transmissive liquid crystal device 350B.

Since the endoscope system 100B uses the transmissive liquid crystal device 350B for changing the light quantity distribution of illumination light, the endoscope system 100B is configured such that the illumination light emitted from the light source unit 320 travels without the optical path of the illumination light being deflected, and travels toward the entrance end IE of the light guide 232.

The transmissive liquid crystal device 350B includes a plurality of cells that are arranged in a matrix and can individually switch transmission/shielding of light. Each cell of the transmissive liquid crystal device 350B can be switched between at least two states, i.e. a first state in which the cell transmits entering illumination light to bring it into the light guide 232, and a second state in which the cell absorbs entering illumination light without transmitting it. Further, the cell can not only switch transmission/shielding, but can also continuously change the transmittance of illumination light.

Although the transmissive liquid crystal device 350B includes members used in an ordinal liquid crystal device, such as a polarization filter configured to adjust a polarization state of entering illumination light, the depiction of such members is omitted in FIG. 18 for the purpose of simplicity.

By using the transmissive liquid crystal device 350B in this manner, not only the transmission and shielding, but also the transmission light quantity between the transmission and the shielding can be set. As regards the light quantity adjustment, not only the control by the time (the time of the transmissive state) and the distribution (the ratio of cells that are in the transmissive state in the area), but also the control by the transmittance can be executed.

Although the example in which the transmissive liquid crystal device 350B has been described here, the embodiments are not limited to this. A reflective liquid crystal device can also be used. In the reflective liquid crystal device, each cell can be switched between at least two states, i.e. a first state in which the cell reflects entering illumination light to bring it into the light guide 232, and a second state in which the cell absorbs entering illumination light without reflecting. Further, the cell can not only switch reflection/shielding, but can also continuously change the reflectance of illumination light. By using the reflective liquid crystal device, the degree of freedom of design of the light source box 310 is improved.

The above-described embodiments are merely examples, and, needless to say, various modifications can be made without departing from the spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source apparatus comprising:
    a light source that is optically connectable to a scope, the scope including a light guide configured to guide light, the light guide having a first illumination light emission end and a second illumination light emission end separately formed from the first illumination light emission end, the light guide being configured to radiate illumination light based on the guided light on a subject;
    a digital mirror having a plurality of movable mirrors disposed in an optical path of the light emitted from the light source, and
    a controller configured to control a light quantity of the light brought to each of the first illumination light emission end and the second illumination light emission end, so as to change a light quantity distribution of the illumination light radiated on the subject;
    wherein the controller controls the plurality of movable mirrors to change the light quantity distribution to adjust first illumination light emitted from the first illumination light emission end and to adjust second illumination light emitted from the second illumination light emission end;
    the controller is configured to derive light distribution correction information, based on an image acquired by an image sensor configured to acquire an image of an observation target, the controller being configured to derive control information of the digital mirror, based on a luminance distribution of the image; and
    the controller is configured to divide the image into a first illumination region in which the first illumination light is dominant, a second illumination region in which the second illumination light is dominant, and a common illumination region in which the first illumination light and the second illumination light are in substantially equal degrees, and to derive the control information of the digital mirror, based on a relationship of luminance values among the first illumination region, the second illumination region, and the common illumination region.

2. The light source apparatus of claim 1, wherein
    the light guide includes a first optical fiber group optically connected to the first illumination light emission end, and a second optical fiber group optically connected to the second illumination light emission end, and
    the digital mirror controls a first light quantity of the first illumination light that travels through a first illumination light selection area corresponding to an entrance end of the first optical fiber group, and a second light quantity of the second illumination light that travels through a second illumination light selection area corresponding to an entrance end of the second optical fiber group.

3. The light source apparatus of claim 2, wherein
    each of the plurality of movable mirrors is switchable between a first state bringing entering light into the light guide, and a second state diverting entering light from the light guide, and
    the controller is configured to control a state of a first mirror group comprising first mirrors located in the first illumination light selection area, and control a state of a second mirror group comprising second mirrors located in the second illumination light selection area.

4. The light source apparatus of claim 3, wherein the digital mirror is configured to change the light quantity distribution of the illumination light by a ratio of mirrors that are in the first state, among the first mirrors included in the first mirror group, and a ratio of mirrors that are in the first state, among the second mirrors included in the second mirror group.

5. The light source apparatus of claim 2, wherein the scope includes a memory configured to store optical fiber group entrance end/exit end distribution information that is distribution information between the entrance end of the first optical fiber group and the entrance end of the second optical fiber group at an entrance end of the light guide, and/or digital mirror control information that is information of an arrangement relationship between the plurality of movable mirrors of the digital mirror and an exit end of the light guide, the optical fiber group entrance end/exit end distribution information and/or the digital mirror control information being transmitted to the light source apparatus when the scope is connected to a main body including the light source apparatus.

6. The light source apparatus of claim 1, wherein the digital mirror is configured to divide an illumination light radiation area into illumination light selection areas, to control a light quantity with respect to each of the illumination light selection areas, and to bring the light into the light guide.

7. The light source apparatus of claim 6, wherein
the illumination light selection areas include a first illumination light selection area configured to emit the first illumination light from the first illumination light emission end, and a second illumination light selection area configured to emit the second illumination light from the second illumination light emission end, and
the digital mirror is configured to selectively control the first illumination light selection area and the second illumination light selection area, thereby controlling the light quantity of the light brought into each of the first illumination light emission end and the second illumination light emission end.

8. The light source apparatus of claim 1, wherein the controller is configured to derive the control information of the digital mirror, based on a luminance value of a shadow appearing in a projection portion or a recess portion of an observation target existing in the common illumination region.

9. A light source apparatus comprising:
a light source that is optically connectable to a scope, the scope including a light guide configured to guide light, the light guide having a first illumination light emission end and a second illumination light emission end separately formed from the first illumination light emission end, the light guide being configured to radiate illumination light based on the guided light on a subject;
a digital mirror having a plurality of movable mirrors disposed in an optical path of the light emitted from the light source, and
a controller configured to control a light quantity of the light brought to each of the first illumination light emission end and the second illumination light emission end, so as to change a light quantity distribution of the illumination light radiated on the subject;
wherein the controller controls the plurality of movable mirrors to change the light quantity distribution to adjust first illumination light emitted from the first illumination light emission end and to adjust second illumination light emitted from the second illumination light emission end;
wherein the controller is configured to:
derive light distribution correction information, based on an image acquired by an image sensor configured to acquire an image of an observation target,
extract, as a correction target region, a region having a luminance exceeding a predetermined threshold on an image,
control digital mirror to change a light quantity of illumination light radiated on the correction target region; and
compare a first image and a second image that are at least two images in different states of the digital mirror, and to extract a region where a luminance distribution is different as a luminance distribution change region, to correlate a difference between a first image state and a second image state and the luminance distribution change region, the first image state being a state of the digital mirror at a time of capturing the first image, the second image state being a state of the digital mirror at a time of capturing the second image, and to derive the light distribution correction information that is a state of the digital mirror necessary for correcting the correction target region.

10. The light source apparatus of claim 9, wherein
each of the plurality of movable mirrors is switchable between at least two states including a first state in which an individual mirror of the plurality of movable mirrors brings entering light into the light guide, and a second state in which the individual mirror brings entering light in a predetermined direction other than a direction toward an entrance end of the light guide, and
the controller is configured to derive light distribution correction information that is arrangement information of the plurality of movable mirrors whose states are to be switched.

11. The light source apparatus of claim 10, wherein the controller is configured to adjust a ratio included in the light distribution correction information between the first state and the second state of mirrors of the plurality of movable mirrors existing in a region on the image with the luminance value exceeding the predetermined threshold, based on a degree of exceeding of the threshold.

12. The light source apparatus of claim 9, wherein the controller includes a machine learning algorithm, and is configured to perform a process of correlating the luminance distribution change region with the first image state and the second image state through the machine learning algorithm, and to derive the light distribution correction information.

13. The light source apparatus of claim 9, wherein the scope includes a memory configured to store optical fiber group entrance end/exit end distribution information that is distribution information between an entrance end of a first optical fiber group and an entrance end of a second optical fiber group at an entrance end of the light guide, and/or digital mirror control information that is information of an arrangement relationship between the plurality of movable mirrors of the digital mirror and an exit end of the light guide, the optical fiber group entrance end/exit end distribution information and/or the digital mirror control information being transmitted to the light source apparatus when the scope is connected to a main body including the light source apparatus.

14. An endoscope system comprising:
a scope including a light guide configured to guide light, and a first illumination light emission unit and a second illumination light emission unit configured to radiate the illumination light based on the guided light; and
the light source apparatus of claim 1.

* * * * *